US008575146B2

(12) United States Patent
Coutre

(10) Patent No.: US 8,575,146 B2
(45) Date of Patent: Nov. 5, 2013

(54) PHARMACEUTICAL USES OF STAUROSPORINE DERIVATIVES

(75) Inventor: Steven Coutre, Stanford, CA (US)

(73) Assignee: Novartis AG, Basel (CH)

( * ) Notice: Subject to any disclaimer, the term of this patent is extended or adjusted under 35 U.S.C. 154(b) by 1911 days.

(21) Appl. No.: 10/560,669

(22) PCT Filed: Jun. 17, 2004

(86) PCT No.: PCT/EP2004/006562
§ 371 (c)(1),
(2), (4) Date: Mar. 23, 2007

(87) PCT Pub. No.: WO2004/112794
PCT Pub. Date: Dec. 29, 2004

(65) Prior Publication Data
US 2007/0299049 A1    Dec. 27, 2007

Related U.S. Application Data

(60) Provisional application No. 60/479,575, filed on Jun. 18, 2003.

(51) Int. Cl.
*A01N 43/00* (2006.01)
*A61K 31/00* (2006.01)
*C07D 273/00* (2006.01)
*C07D 285/36* (2006.01)

(52) U.S. Cl.
USPC ..................................... 514/211.08; 540/545

(58) Field of Classification Search
USPC ..................................... 514/211.08; 540/545
See application file for complete search history.

(56) References Cited

U.S. PATENT DOCUMENTS

| | | | |
|---|---|---|---|
| 4,639,455 A | | 1/1987 | Moore |
| 5,093,330 A | * | 3/1992 | Caravatti et al. ......... 514/211.08 |
| 2002/0061873 A1 | * | 5/2002 | Matthews et al. ........ 514/211.08 |
| 2007/0213317 A1 | | 9/2007 | Buchdunger et al. |

FOREIGN PATENT DOCUMENTS

| | | |
|---|---|---|
| EP | 0470490 | 2/1992 |
| EP | 0518468 | 12/1992 |
| JP | 63295589 | 12/1988 |
| WO | WO9631514 | 10/1996 |
| WO | WO9749406 | 12/1997 |
| WO | WO9848795 | 11/1998 |
| WO | WO9962537 | 12/1999 |
| WO | WO0246197 | 6/2002 |
| WO | WO02080925 | 10/2002 |
| WO | WO03037347 | 5/2003 |
| WO | WO03065995 | 8/2003 |
| WO | WO2004091663 | 10/2004 |
| WO | WO2004093910 | 11/2004 |

OTHER PUBLICATIONS

Goekjian et al. Expert Opinions on Investigational Drugs. 2001, vol. 10, No. 12, pp. 2117-2140.*
Ma et al. Blood, Mar. 2002, vol. 99, No. 5, pp. 1741-1744.*
Amon, Ulrich et al., "CGP 41251, a Novel Protein . . . ", Pharmacology, vol. 47, pp. 200-208, 1993.
Kurosawa, M. et al., "Effect of stauorsporine on . . . ", Annals of Allergy, vol. 63. pp. 231-232, Sep. 1989.
International Search Report dated Sep. 30, 2004.
International Search Report dated Apr. 5, 2005.
Opdal, Suri H. et al, "New insight into sudden . . . ", The Lancet, vol. 364, No. 9437, pp. 825-826, Sep. 4, 2004.
Wark, Peter A. B. et al., "Allergic bronchopulmonary aspergillosis: New concepts . . . ", Respirology, vol. 6, pp. 1-7, Mar. 2001.
Greenberger, Paul A, "Clinical Aspects of Allergic Bronchopulmonary . . . ", Frontiers in Bioscience, vol. 8, pp. 119-127, Jan. 1, 2003.
Svirschchevskaya E V et al., "Immunotherapy of allergic bronchopulmonary . . . ", Frontiers in Bioscience, vol. 8, pp. 92-101, Jan. 1, 2003.
Bradshaw, D et al., "Theraeutic potential of protein . . . ", Agents Actions, vol. 38, pp. 135-147, 1993.
Hudson, Steven J. et al., "Intracelluar signaling of tumor necrosis . . . ", Jounal of Neuroimmunology, vol. 70, pp. 199-206, 1996.
Jurewicz, A. et al., "Shedding of TNF receptors in . . . ", Neurology, vol. 53, No. 7, pp. 1409-1414, Oct. 22, 1999.
Longley, B. J. et al., "New approaches to therapy . . . ", Hemotology/Oncology clinics of North America, vol. 14, No. 3, Jun. 2000.
Tharp, M D, "Mastocytosis", Curr. Probl. Dermatol., vol. 10, No. 5, pp. 181-210, 1998.

* cited by examiner

*Primary Examiner* — Samira Jean-Louis
(74) *Attorney, Agent, or Firm* — Matthew Mulkeen; George Dohmann

(57) ABSTRACT

This application relates to the use of staurosporines derivatives for the curative, palliative or prophylactic treatment of allergic rhinitis, allergic dermatitis, drug allergy or food allergy, angioedema, urticaria, sudden infant death syndrome, bronchopulmonary aspergillosis, multiple sclerosis, or mastocytosis; and to a method of treatment of warm-blooded animals in which a therapeutically effective dose of a compound of a Staurosporine Derivative is administered to a warm-blooded animal suffering from one of the diseases or conditions mentioned above.

19 Claims, No Drawings

PHARMACEUTICAL USES OF STAUROSPORINE DERIVATIVES

This application is the National Stage of International Application No. PCT/EP04/006562, filed on Jun. 17, 2004, which claims benefit under 35 U.S.C. §119(e) of U.S. Provisional Application No. 60/479,575, filed on Jun. 18, 2003. The contents of both are incorporated herein by reference in their entirety.

The present invention relates to the use of staurosporine derivatives (hereinafter: "STAUROSPORINE DERIVATIVES") in free form or in pharmaceutically acceptable salt form in the manufacture of a pharmaceutical composition for the curative, palliative or prophylactic treatment of allergic rhinitis, allergic dermatitis, drug allergy or food allergy, angioedema, urticaria, sudden infant death syndrome, bronchopulmonary aspergillosis, multiple sclerosis, or mastocytosis; and to a method of treatment of warm-blooded animals, preferably humans, in which a therapeutically effective dose of a compound of of a STAUROSPORINE DERIVATIVE is administered to a warm-blooded animal suffering from one of the diseases or conditions mentioned above.

The invention relates in particular to the use of staurosporines derivatives of formula

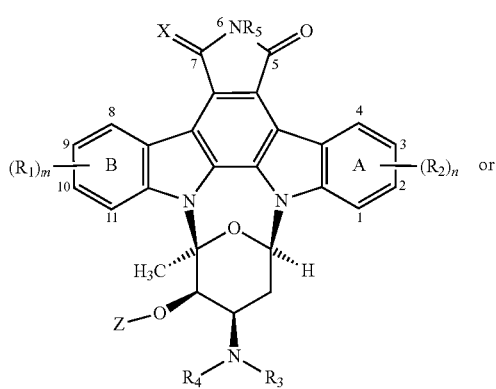

(I)

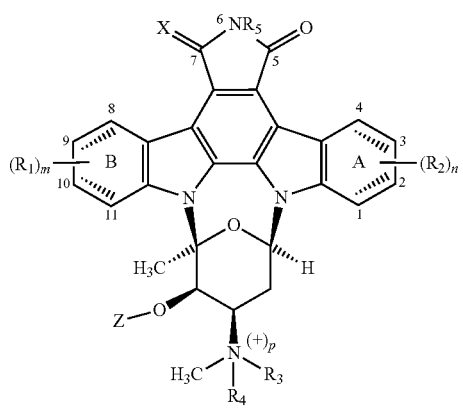

(II)

wherein (II) is the partially hydrogenated derivative of compound (I),

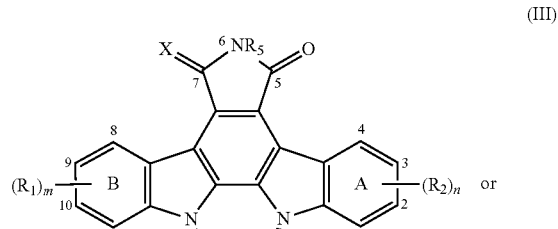

(III)

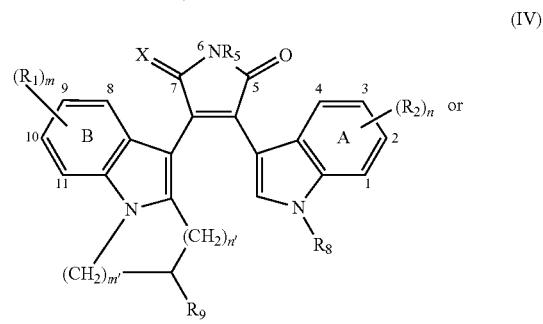

(IV)

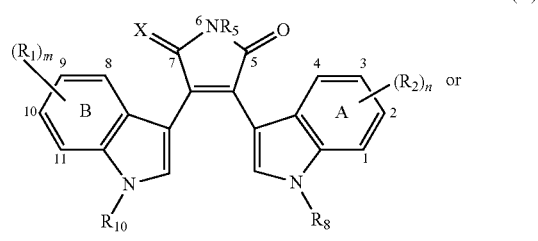

(V)

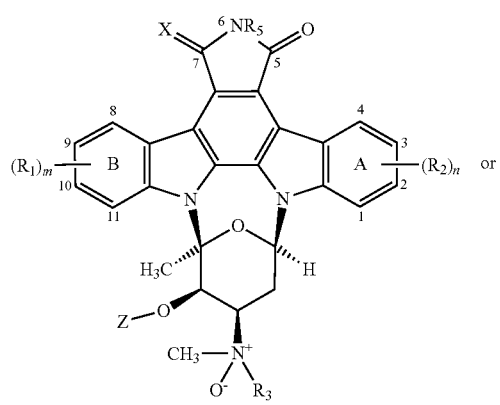

(VI)

wherein $R_1$ and $R_2$, are, independently of one another, unsubstituted or substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

n and m are, independently of one another, a number from and including 0 to and including 4;

n' and m' are, independently of one another, a number from and including 0 to and including 4;

$R_3$, $R_4$, $R_8$ and $R_{10}$ are, independently of one another, hydrogen, —O—, acyl with up to 30 carbon atoms, an aliphatic, carbocyclic, or carbocyclic-aliphatic radical with up to 29 carbon atoms in each case, a heterocyclic or heterocyclic-aliphatic radical with up to 20 carbon atoms in each case, and in each case up to 9 heteroatoms, an acyl with up to 30 carbon atoms, wherein $R_4$ may also be absent;

or if $R_3$ is acyl with up to 30 carbon atoms, $R_4$ is not an acyl; p is 0 if $R_4$ is absent, or is 1 if $R_3$ and $R_4$ are both present and in each case are one of the aforementioned radicals;

$R_5$ is hydrogen, an aliphatic, carbocyclic, or carbocyclic-aliphatic radical with up to 29 carbon atoms in each case, or a heterocyclic or heterocyclic-aliphatic radical with up to 20 carbon atoms in each case, and in each case up to 9 heteroatoms, or acyl with up to 30 carbon atoms;

$R_7$, $R_8$ and $R_9$ are acyl or -(lower alkyl)-acyl, unsubstituted or substituted alkyl, hydrogen, halogen, hydroxy, etherified or esterified hydroxy, amino, mono- or disubstituted amino, cyano, nitro, mercapto, substituted mercapto, carboxy,carbonyl, carbonyidioxy, esterified carboxy, carbamoyl, N-mono- or N,N-di-substituted carbamoyl, sulfo, substituted sulfonyl, aminosulfonyl or N-mono- or N,N-di-substituted aminosulfonyl;

X stands for 2 hydrogen atoms; for 1 hydrogen atom and hydroxy; for O; or for hydrogen and lower alkoxy;

Z stands for hydrogen or lower alkyl;

and either the two bonds characterised by wavy lines are absent in ring A and replaced by 4 hydrogen atoms, and the two wavy lines in ring B each, together with the respective parallel bond, signify a double bond;

or the two bonds characterised by wavy lines are absent in ring B and replaced by a total of 4 hydrogen atoms, and the two wavy lines in ring A each, together with the respective parallel bond, signify a double bond;

or both in ring A and in ring B all of the 4 wavy bonds are absent and are replaced by a total of 8 hydrogen atoms;

or a salt thereof, if at least one salt-forming group is present for the preparation of a pharmaceutical composition for the treatment of FIP1L1-PDGFRα-induced myeloproliferative diseases.

The general terms and definitions used hereinbefore and hereinafter preferably have the following meanings:

The prefix "lower" indicates that the associated radical preferably has up to and including a maximum of 7 carbon atoms, especially up to and including a maximum of 4 carbon atoms.

Lower alkyl is especially methyl, ethyl, n-propyl, isopropyl, n-butyl, isobutyl, sec-butyl, or tert-butyl, and also pentyl, hexyl, or heptyl.

Unsubstituted or substituted alkyl is preferably $C_1$-$C_{20}$alkyl, especially lower alkyl, typically methyl, ethyl, n-propyl, isopropyl, n-butyl, isobutyl, sec-butyl, or tert-butyl, which is unsubstituted or substituted especially by halogen, such as fluorine, chlorine, bromine, or iodine, $C_6$-$C_{14}$aryl, such as phenyl or naphthyl, hydroxy, etherified hydroxy, such as lower alkoxy, phenyl-lower alkoxy or phenyloxy, esterified hydroxy, such as lower alkanoyloxy or benzoyloxy, amino, mono- or disubstituted amino, such as lower alkylamino, lower alkanoylamino, phenyl-lower alkylamino, N,N-di-lower alkylamino, N,N-di-(phenyl-lower alkyl)amino, cyano, mercapto, substituted mercapto, such as lower alkylthio, carboxy, esterified carboxy, such as lower alkoxycarbonyl, carbamoyl, N-mono- or N,N-disubstituted carbamoyl, such as N-lower alkylcarbamoyl or N,N-di-lower alkylcarbamoyl, sulfo, substituted sulfo, such as lower alkanesulfonyl or lower alkoxysulfonyl, aminosulfonyl or N-mono- or N,N-disubstituted aminosulfonyl, such as N-lower alkylaminosulfonyl or N,N-di-lower alkylaminosulfonyl.

Halogen is preferably fluorine, chlorine, bromine, or iodine, especially fluorine or chlorine.

Etherified hydroxy is especially lower alkoxy, $C_6$-$C_{14}$aryloxy, such as phenyloxy, or $C_6$-$C_{14}$aryl-lower alkoxy, such as benzyloxy.

Etherified hydroxy is preferably lower alkanoyloxy or $C_6$-$C_{14}$arylcarbonyloxy, such as benzoyloxy.

Mono- or disubstituted amino is especially amino monosubstituted or disubstituted by lower alkyl, $C_6$-$C_{14}$aryl, $C_6$-$C_{14}$aryl-lower alkyl, lower alkanoyl, or $C_6$-$C_{12}$arylcarbonyl.

Substituted mercapto is especially lower alkylthio, $C_6$-$C_{14}$arylthio, $C_6$-$C_{14}$aryl-lower alkylthio, lower alkanoylthio, or $C_6$-$C_{14}$aryl-lower alkanoylthio.

Esterified carboxy is especially lower alkoxycarbonyl, $C_6$-$C_{14}$aryl-lower alkoxycarbonyl or $C_6$-$C_{14}$aryloxycarbonyl.

N-Mono- or N,N-disubstituted carbamoyl is especially carbamoyl N-monosubstituted or N,N-disubstituted by lower alkyl, $C_6$-$C_{14}$aryl or $C_6$-$C_{14}$aryl-lower alkyl.

Substituted sulfonyl is especially $C_6$-$C_{14}$arylsulfonyl, such as toluenesulfonyl, $C_6$-$C_{14}$aryl-lower alkanesulfonyl or lower alkanesulfonyl.

N-Mono- or N,N-disubstituted aminosulfonyl is especially aminosulfonyl N-monosubstituted or N,N-disubstituted by lower alkyl, $C_6$-$C_{14}$aryl or $C_6$-$C_{14}$aryl-lower alkyl.

$C_6$-$C_{14}$Aryl is an aryl radical with 6 to 14 carbon atoms in the ring system, such as phenyl, naphthyl, fluorenyl, or indenyl, which is unsubstituted or is substituted especially by halogen, such as fluorine, chlorine, bromine, or iodine, phenyl or naphthyl, hydroxy, lower alkoxy, phenyl-lower alkoxy, phenyloxy, lower alkanoyloxy, benzoyloxy, amino, lower alkylamino, lower alkanoylamino, phenyl-lower alkylamino, N,N-di-lower alkylamino, N,N-di-(phenyl-lower alkyl) amino, cyano, mercapto, lower alkylthio, carboxy, lower alkoxycarbonyl, carbamoyl, N-lower alkylcarbamoyl, N,N-di-lower alkylcarbamoyl, sulfo, lower alkanesulfonyl, lower alkoxysulfonyl, aminosulfonyl, N-lower alkylaminosulfonyl, or N,N-di-lower alkylaminosulfonyl.

The indices n and m are in each case preferably 1, 2 or especially 0. In general, compounds of formula I in which n and m are in each case 0 (zero) are especially preferred.

An aliphatic carbohydrate radical $R_3$, $R_4$, $R_8$ or $R_{10}$ with up to 29 carbon atoms, which is substituted by acyclic substituents and preferably has a maximum of 18, especially a maximum of 12, and as a rule not more than 7 carbon atoms, may be saturated or unsaturated and is especially an unsubstituted or a straight-chain or branched lower alkyl, lower alkenyl, lower alkadienyl, or lower alkinyl radical substituted by acyclic substituents. Lower alkyl is, for example, methyl, ethyl, n-propyl, isopropyl, n-butyl, isobutyl, sec-butyl or tert-butyl, and also n-pentyl, isopentyl, n-hexyl, isohexyl and n-heptyl; lower alkenyl is, for example, allyl, propenyl, isopropenyl, 2- or 3-methallyl and 2- or 3-butenyl; lower alkadienyl is, for example, 1-penta-2,4-dienyl; lower alkinyl is, for example, propargyl or 2-butinyl. In corresponding unsaturated radicals, the double bond is especially located in a position higher than the α-position in relation to the free valency. Substituents are especially the acyl radicals defined hereinbelow as substituents of R°, preferably free or esterified carboxy, such as carboxy or lower alkoxycarbonyl, cyano or di-lower alkylamino.

A carbocyclic or carbocyclic-aliphatic radical $R_3$, $R_4$, $R_8$ or $R_{10}$ with up to 29 carbon atoms in each case is especially an aromatic, a cycloaliphatic, a cycloaliphatic-aliphatic, or an aromatic-aliphatic radical which is either present in unsubstituted form or substituted by radicals referred to hereinbelow as substituents of $R°$. An aromatic radical (aryl radical) $R_3$ or $R_4$ is most especially a phenyl, also a naphthyl, such as 1- or 2-naphthyl, a biphenylyl, such as especially 4-biphenylyl, and also an anthryl, fluorenyl and azulenyl, as well as their aromatic analogues with one or more saturated rings, which is either present in unsubstituted form or substituted by radicals referred to hereinbelow as substituents of $R°$. Preferred aromatic-aliphatic radicals are aryl-lower alkyl- and aryl-lower alkenyl radicals, e.g. phenyl-lower alkyl or phenyl-lower alkenyl with a terminal phenyl radical, such as for example benzyl, phenethyl, 1-, 2-, or 3-phenylpropyl, diphenylmethyl (benzhydryl), trityl, and cinnamyl, and also 1- or 2-naphthylmethyl. Of aryl radicals carrying acyclic radicals, such as lower alkyl, special mention is made of o-, m- and p-tolyl and xylyl radicals with variously situated methyl radicals.

A cycloaliphatic radical $R_3$, $R_4$, $R_8$ or $R_{10}$ with up to 29 carbon atoms is especially a substituted or preferably unsubstituted mono-, bi-, or polycyclic cycloalkyl-, cycloalkenyl-, or cycloalkadienyl radical. Preference is for radicals with a maximum of 14, especially 12, ring-carbon atoms and 3- to 8-, preferably 5- to 7-, and most especially 6-member rings which can also carry one or more, for example two, aliphatic hydrocarbon radicals, for example those named above, especially the lower alkyl radicals, or other cycloaliphatic radicals as substituents. Preferred substituents are the acyclic substituents named hereinbelow for $R°$.

A cycloaliphatic-aliphatic radical $R_3$, $R_4$, $R_8$ or $R_{10}$ with up to 29 carbon atoms is a radical in which an acyclic radical, especially one with a maximum of 7, preferably a maximum of 4 carbon atoms, such as especially methyl, ethyl, and vinyl, carries one or more cycloaliphatic radicals as defined hereinabove. Special mention is made of cycloalkyl-lower alkyl- radicals, as well as their analogues which are unsaturated in the ring and/or in the chain, but are non-aromatic, and which carry the ring at the terminal carbon atom of the chain. Preferred substituents are the acyclic substituents named herein below for $R°$.

Heterocyclic radicals $R_3$, $R_4$, $R_8$ or $R_{10}$ with up to 20 carbon atoms each and up to 9 heteroatoms each are especially monocyclic, but also bi- or polycyclic, aza-, thia-, oxa-, thiaza-, oxaza-, diaza-, triaza-, or tetrazacyclic radicals of an aromatic character, as well as corresponding heterocyclic radicals of this type which are partly or most especially wholly saturated, these radicals—if need be—possibly carrying further acyclic, carbocyclic, or heterocyclic radicals and/or possibly mono-, di-, or polysubstituted by functional groups, preferably those named hereinabove as substituents of aliphatic hydrocarbon radicals. Most especially they are unsubstituted or substituted monocyclic radicals with a nitrogen, oxygen, or sulfur atom, such as 2-aziridinyl, and especially aromatic radicals of this type, such as pyrryl, for example 2-pyrryl or 3-pyrryl, pyridyl, for example 2-, 3-, or 4-pyridyl, and also thienyl, for example 2- or 3-thienyl, or furyl, for example 2-furyl; analogous bicyclic radicals with an oxygen, sulfur, or nitrogen atom are, for example, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, or benzothienyl, typically 2- or 3-benzothienyl; preferred monocyclic and bicyclic radicals with several heteroatoms are, for example, imidazolyl, typically 2- or 4-imidazolyl, pyrimidinyl, typically 2- or 4-pyrimidinyl, oxazolyl, typically 2-oxazolyl, isoxazolyl, typically 3-isoxazolyl, or thiazolyl, typically 2-thiazolyl, and benzimidazolyl, typically 2-benzimidazolyl, benzoxazolyl, typically 2-benzoxazolyl, or quinazolyl, typically 2-quinazolinyl. Appropriate partially or, especially, completely saturated analogous radicals may also be considered, such as 2-tetrahydrofuryl, 2- or 3-pyrrolidinyl, 2-, 3-, or 4-piperidyl, and also 2- or 3-morpholinyl, 2- or 3-thiomorpholinyl, 2-piperazinyl and N-mono- or N,N'-bis-lower alkyl-2-piperazinyl radicals. These radicals may also carry one or more acyclic, carbocyclic, or heterocyclic radicals, especially those mentioned hereinabove. The free valency of the heterocyclic radicals $R_3$ or $R_4$ must emanate from one of their carbon atoms. Heterocyclyl may be unsubstituted or substituted by one or more, preferably one or two, of the substituents named hereinbelow for $R°$.

Heterocyclic-aliphatic radicals $R_3$, $R_4$, $R_8$ or $R_{10}$ especially lower alkyl radicals, especially with a maximum of 7, preferably a maximum of 4 carbon atoms, for example those named hereinabove, which carry one, two, or more heterocyclic radicals, for example those named in the preceding paragraph, the heterocyclic ring possibly being linked to the aliphatic chain also by one of its nitrogen atoms. A preferred heterocyclic-aliphatic radical $R_1$ is, for example, imidazol-1-ylmethyl, 4-methylpiperazin-1-ylmethyl, piperazin-1-ylmethyl, 2-(morpholin-4-yl)ethyl and also pyrid-3-ylmethyl. Heterocyclyl may be unsubstituted or substituted by one or more, preferably one or two, of the substituents named hereinbelow for $R°$.

A heteroaliphatic radical $R_3$, $R_4$, $R_8$ or $R_{10}$ with up to 20 carbon atoms each and up to 10 heteroatoms each is an aliphatic radical which, instead of one, two, or more carbon atoms, contains identical or different heteroatoms, such as especially oxygen, sulfur, and nitrogen. An especially preferred arrangement of a heteroaliphatic radical $R_1$ takes the form of oxa-alkyl radicals in which one or more carbon atoms are replaced in a preferably linear alkyl by oxygen atoms preferably separated from one another by several (especially 2) carbon atoms so that they form a repeating group, if need be multi-repeating group $(O-CH_2-CH_2-)_q$, wherein q=1 to 7.

Especially preferred as $R_3$, $R_4$, $R_8$ or $R_{10}$, apart from acyl, is lower alkyl, particularly methyl or ethyl; lower alkoxycarbonyl-lower alkyl, especially methoxycarbonylmethyl or 2-(tert-butoxycarbonyl)ethyl; carboxy-lower alkyl, especially carboxymethyl or 2-carboxyethyl; or cyano-lower alkyl, especially 2-cyanoethyl.

An acyl radical $R_3$, $R_4$, $R_6$, $R_7$, $R_8$, $R_9$, or $R_{10}$ with up to 30 carbon atoms derives from a carboxylic acid, functionally modified if need be, an organic sulfonic acid, or a phosphoric acid, such as pyro- or orthophosphoric acid, esterified if need be.

An acyl designated $Ac^1$ and derived from a carboxylic acid, functionally modified if need be, is especially one of the subformula $Y-C(=W)-$, wherein W is oxygen, sulfur, or imino and Y is hydrogen, hydrocarbyl $R°$ with up to 29 carbon atoms, hydrocarbyloxy $R°-O-$, an amino group or a substituted amino group, especially one of the formula $R°HN-$ or $R°R°N-$ (wherein the $R°$ radicals may be identical or different from one another).

The hydrocarbyl (hydrocarbon radical) $R°$ is an acyclic (aliphatic), carbocyclic, or carbocyclic-acyclic hydrocarbon radical, with up to 29 carbon atoms each, especially up to 18, and preferably up to 12 carbon atoms, and is saturated or unsaturated, unsubstituted or substituted. Instead of one, two, or more carbon atoms, it may contain identical or different heteroatoms, such as especially oxygen, sulfur, and nitrogen in the acyclic and/or cyclic part; in the latter case, it is described as a heterocyclic radical (heterocyclyl radical) or a heterocyclic-acyclic radical.

Unsaturated radicals are those, which contain one or more, especially conjugated and/or isolated, multiple bonds (double or triple bonds). The term cyclic radicals includes also aromatic and non-aromatic radicals with conjugated double bonds, for example those wherein at least one 6-member carbocyclic or a 5- to 8-member heterocyclic ring contains the maximum number of non-cumulative double bonds. Carbocyclic radicals, wherein at least one ring is present as a 6-member aromatic ring (i.e. a benzene ring), are defined as aryl radicals.

An acyclic unsubstituted hydrocarbon radical $R^o$ is especially a straight-chained or branched lower alkyl-, lower alkenyl-, lower alkadienyl-, or lower alkinyl radical. Lower alkyl $R^o$ is, for example, methyl, ethyl, n-propyl, isopropyl, n-butyl, isobutyl, sec-butyl or tert-butyl, and also n-pentyl, isopentyl, n-hexyl, isohexyl and n-heptyl; lower alkenyl is, for example, allyl, propenyl, isopropenyl, 2- or 3-methallyl and 2- or 3-butenyl; lower alkadienyl is, for example, 1-penta-2,4-dienyl; lower alkinyl is, for example, propargyl or 2-butinyl. In corresponding unsaturated radicals, the double bond is especially located in a position higher than the α-position in relation to the free valency.

A carbocyclic hydrocarbon radical $R^o$ is especially a mono-, bi-, or polycyclic cycloalkyl-, cycloalkenyl-, or cycloalkadienyl radical, or a corresponding aryl radical. Preference is for radicals with a maximum of 14, especially 12, ring-carbon atoms and 3- to 8-, preferably 5- to 7-, and most especially 6-member rings which can also carry one or more, for example two, acyclic radicals, for example those named above, especially the lower alkyl radicals, or other carbocyclic radicals. Carbocyclic-acyclic radicals are those in which an acyclic radical, especially one with a maximum of 7, preferably a maximum of 4 carbon atoms, such as especially methyl, ethyl and vinyl, carries one or more carbocyclic, if need be aromatic radicals of the above definition. Special mention is made of cycloalkyl-lower and aryl-lower alkyl radicals, as well as their analogues which are unsaturated in the ring and/or chain, and which carry the ring at the terminal carbon atom of the chain.

Cycloalkyl $R^o$ has most especially from 3 up to and including 10 carbon atoms and is, for example, cyclopropyl, cyclobutyl, cyclopentyl, cyclohexyl, cycloheptyl, and cyclooctyl, as well as bicyclo[2,2,2]octyl, 2-bicyclo[2,2,1]heptyl, and adamantyl, which may also be substituted by 1, 2, or more, for example lower, alkyl radicals, especially methyl radicals; cycloalkenyl is for example one of the monocyclic cycloalkyl radicals already named which carries a double bond in the 1-, 2-, or 3 position. Cycloalkyl-lower alkyl or -lower alkenyl is for example a -methyl, -1- or -2-ethyl, -1- or -2-vinyl, -1-, -2-, or -3-propyl or -allyl substituted by one of the above-named cycloalkyl radicals, those substituted at the end of the linear chain being preferred.

An aryl radical $R^o$ is most especially a phenyl, also a naphthyl, such as 1- or 2-naphthyl, a biphenylyl, such as especially 4-biphenylyl, and also an anthryl, fluorenyl and azulenyl, as well as their aromatic analogues with one or more saturated rings. Preferred aryl-lower alkyl and -lower alkenyl radicals are, for example, phenyl-lower alkyl or phenyl-lower alkenyl with a terminal phenyl radical, such as for example benzyl, phenethyl, 1-, 2-, or 3-phenylpropyl, diphenylmethyl (benzhydryl), trityl, and cinnamyl, and also 1- or 2-naphthylmethyl. Aryl may be unsubstituted or substituted.

Heterocyclic radicals, including heterocyclic-acyclic radicals, are especially monocyclic, but also bi- or polycyclic, aza-, thia-, oxa-, thiaza-, oxaza-, diaza-, triaza-, or tetrazacyclic radicals of an aromatic character, as well as corresponding heterocyclic radicals of this type which are partly or most especially wholly saturated; if need be, for example as in the case of the above-mentioned carbocyclic or aryl radicals, these radicals may carry further acyclic, carbocyclic, or heterocyclic radicals and/or may be mono-, di-, or polysubstituted by functional groups. The acyclic part in heterocyclic-acyclic radicals has for example the meaning indicated for the corresponding carbocyclic-acyclic radicals. Most especially they are unsubstituted or substituted monocyclic radicals with a nitrogen, oxygen, or sulfur atom, such as 2-aziridinyl, and especially aromatic radicals of this type, such as pyrrolyl, for example 2-pyrrolyl or 3-pyrrolyl, pyridyl, for example 2-, 3-, or 4-pyridyl, and also thienyl, for example 2- or 3-thienyl, or furyl, for example 2-furyl; analogous bicyclic radicals with an oxygen, sulfur, or nitrogen atom are, for example, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, or benzothienyl, typically 2- or 3-benzothienyl; preferred monocyclic and bicyclic radicals with several heteroatoms are, for example, imidazolyl, typically 2-imidazolyl, pyrimidinyl, typically 2- or 4-pyrimidinyl, oxazolyl, typically 2-oxazolyl, isoxazolyl, typically 3-isoxazolyl, or thiazolyl, typically 2-thiazolyl, and benzimidazolyl, typically 2-benzimidazolyl, benzoxazolyl, typically 2-benzoxazolyl, or quinazolyl, typically 2-quinazolinyl. Appropriate partially or, especially, completely saturated analogous radicals may also be considered, such as 2-tetrahydrofuryl, 4-tetrahydrofuryl, 2- or 3-pyrrolidyl, 2-, 3-, or 4-piperidyl, and also 2- or 3-morpholinyl, 2- or 3-thiomorpholinyl, 2-piperazinyl, and N,N'-bis-lower alkyl-2-piperazinyl radicals. These radicals may also carry one or more acyclic, carbocyclic, or heterocyclic radicals, especially those mentioned hereinabove. Heterocyclic-acyclic radicals are especially derived from acyclic radicals with a maximum of 7, preferably a maximum of 4 carbon atoms, for example those named hereinabove, and may carry one, two, or more heterocyclic radicals, for example those named hereinabove, the ring possibly being linked to the aliphatic chain also by one of its nitrogen atoms.

As already mentioned, a hydrocarbyl (including a heterocyclyl) may be substituted by one, two, or more identical or different substituents (functional groups); one or more of the following substituents may be considered: lower alkyl; free, etherified and esterified hydroxyl groups; carboxy groups and esterified carboxy groups; mercapto- and lower alkylthio- and, if need be, substituted phenylthio groups; halogen atoms, typically chlorine and fluorine, but also bromine and iodine; halogen-lower alkyl groups; oxo groups which are present in the form of formyl (i.e. aldehydo) and keto groups, also as corresponding acetals or ketals; azido groups; nitro groups; cyano groups; primary, secondary and preferably tertiary amino groups, amino-lower alkyl, mono- or disubstituted amino-lower alkyl, primary or secondary amino groups protected by conventional protecting groups (especially lower alkoxycarbonyl, typically tert-butoxycarbonyl) lower alkylenedloxy, and also free or functionally modified sulfo groups, typically sulfamoyl or sulfo groups present in free form or as salts. The hydrocarbyl radical may also carry carbamoyl, ureido, or guanidino groups, which are free or which carry one or two substituents, and cyano groups. The above use of the word "groups" is taken to imply also an individual group.

Halogen-lower alkyl contains preferably 1 to 3 halogen atoms; preferred is trifluoromethyl or chloromethyl.

An etherified hydroxyl group present in the hydrocarbyl as substituent is, for example, a lower alkoxy group, typically the methoxy-, ethoxy-, propoxy-, isopropoxy-, butoxy-, and tert-butoxy group, which may also be substituted, especially by (i) heterocyclyl, whereby heterocyclyl can have preferably 4 to 12 ring atoms, may be unsaturated, or partially or wholly saturated, is mono- or bicyclic, and may contain up to three heteroatoms selected from nitrogen, oxygen, and sulfur, and is most especially pyrrolyl, for example 2-pyrrolyl or 3-pyrrolyl, pyridyl, for example 2-, 3- or 4-pyridyl, and also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-2- or 3-morpholinyl, 2- or 3-thiomorpholinyl, 2-piperazinyl or N,N'-bis-lower alkyl-2-piperazinyl; and also (ii) by halogen atoms, for example mono-, di-, or polysubstituted especially in the 2-position, as in the 2,2,2-trichloroethoxy, 2-chloroethoxy, or 2-iodoethoxy radical, or (iii) by hydroxy or (iv) lower alkoxy radicals, each preferably mono-substituted, especially in the 2-position, as in the 2-methoxyethoxy radical. Such etherified hydroxyl groups are also unsubstituted or substituted phenoxy radicals and phenyl-lower alkoxy radicals, such as especially benzyloxy, benzhydryloxy, and triphenylmethoxy(trityloxy), as well as heterocyclyloxy radicals, wherein heterocyclyl can have preferably 4 to 12 ring atoms, may be unsaturated, or partially or wholly saturated, is mono- or bicyclic, and may contain up to three heteroatoms selected from nitrogen, oxygen, and sulfur, and is most especially pyrrolyl, for example 2-pyrrolyl or 3-pyrrolyl, pyridyl, for example 2-, 3- or 4-pyridyl, and also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl; such as especially 2- or 4-tetrahydropyranyloxy.

Etherified hydroxyl groups in this context are taken to include silylated hydroxyl groups, typically for example tri-lower alkylsilyloxy, typically trimethylsilyloxy and dimethyl-tert-butylsilyloxy, or phenyldl-lower alkylsilyloxy and lower alkyl-diphenyisilyloxy.

An esterified hydroxyl group present in the hydrocarbyl as a substituent is, for example, lower alkanoyloxy.

A carboxyl group present in the hydrocarbyl as a substituent is one in which the hydrogen atom is replaced by one of the hydrocarbyl radicals characterised hereinabove, preferably a lower alkyl- or phenyl-lower alkyl radical; an example of an esterified carboxyl group is lower alkoxycarbonyl or phenyl-lower alkoxycarbonyl substituted if need be in the phenyl part, especially the methoxy, ethoxy, tert-butoxy, and benzyloxycarbonyl group, as well as a lactonised carboxyl group.

A primary amino group —$NH_2$ as substituent of the hydrocarbyls may also be present in a form protected by a conventional protecting group. A secondary amino group carries, instead of one of the two hydrogen atoms, a hydrocarbyl radical, preferably an unsubstituted one, typically one of the above-named, especially lower alkyl, and may also be present in protected form.

A tertiary amino group present in the hydrocarbyl as substituent carries 2 different or, preferably, identical hydrocarbyl radicals (including the heterocyclic radicals), such as the unsubstituted hydrocarbyl radicals characterised hereinabove, especially lower alkyl.

A preferred amino group is one with the formula $R_{11}(R_{12})$ N—, wherein $R_{11}$ and $R_{12}$ are independently in each case hydrogen, unsubstituted acyclic $C_1$-$C_7$-hydrocarbyl (such as especially $C_1$-$C_4$alkyl or $C_2$-$C_4$alkenyl) or monocyclic aryl, aralkyl, or aralkenyl, substituted if necessary by $C_1$-$C_4$-alkyl, $C_1$-$C_4$-alkoxy, halogen, and/or nitro, and having a maximum of 10 carbon atoms, where the carbon-containing radicals may be interlinked through a carbon-carbon bond or an oxygen atom, a sulfur atom, or a nitrogen atom substituted if necessary by hydrocarbyl. In such a case, they form a nitrogen-containing heterocyclic ring with the nitrogen atom of the amino group. The following are examples of especially preferred disubstituted amino groups: di-lower alkylamino, typically dimethylamino or diethylamino, pyrrolidino, imidazol-1-yl, piperidino, piperazino, 4-lower alkylpiperazino, morpholino, thiomorpholino and piperazino or 4-methylpiperazino, as well as diphenylamino and dibenzylamino substituted if need be, especially in the phenyl part, for example by lower-alkyl, lower-alkoxy, halogen, and/or nitro; of the protected groups, especially lower alkoxy-carbonylamino, typically tert-butoxycarbonylamino, phenyl-lower alkoxycarbonylamino, typically 4-methoxybenzyloxycarbonylamino, and 9-fluorenylmethoxycarbonylamino.

Amino-lower alkyl is most especially substituted in the 1-position of the lower alkyl chain by amino and is especially aminomethyl.

Mono- or disubstituted amino-lower alkyl is amino-lower alkyl substituted by one or two radicals, wherein amino-lower alkyl is most especially substituted by amino in the 1-position of the lower alkyl chain and is especially aminomethyl; the amino substituents here are preferably (if 2 substituents are present in the respective amino group independently of one another) from the group comprising lower alkyl, such as especially methyl, ethyl or n-propyl, hydroxy-lower alkyl, typically 2-hydroxyethyl, $C_3$-$C_8$cycloalkyl, especially cyclohexyl, amino-lower alkyl, typically 3-aminopropyl or 4-aminobutyl, N-mono- or N,N-di(lower alkyl)-amino-lower alkyl, typically 3-(N,N-dimethylamino)propyl, amino, N-mono- or N,N-di-lower alkylamino and N-mono- or N,N-di-(hydroxy-lower alkyl)amino.

Disubstituted amino-lower alkyl is also a 5 or 6-membered, saturated or unsaturated heterocyclyl bonded to lower alkyl via a nitrogen atom (preferably in the 1-position) and having 0 to 2, especially 0 or 1, other heteroatoms selected from oxygen, nitrogen, and sulfur, which is unsubstituted or substituted, especially by one or two radicals from the group comprising lower alkyl, typically methyl, and also oxo. Preferred here is pyrrolidino (1-pyrrolidinyl), piperidino (1-piperidinyl), piperazino (1-piperazinyl), 4-lower alkylpiperazino, typically 4-methylpiperazino, imidazolino (1-imidazolyl), morpholino (4-morpholinyl), or also thiomorpholino, S-oxo-thiomorpholino, or S,S-dioxothiomorpholino.

Lower alkylenedioxy is especially methylenedioxy.

A carbamoyl group carrying one or two substituents is especially aminocarbonyl(carbamoyl) which is substituted by one or two radicals at the nitrogen; the amino substituents here are preferably (if 2 substituents are present in the respective amino group independently of one another) from the group comprising lower alkyl, such as especially methyl, ethyl or n-propyl, hydroxy-lower alkyl, typically 2-hydroxyethyl, $C_3$-$C_8$cycloalkyl, especially cyclohexyl, amino-lower alkyl, typically 3-aminopropyl or 4-aminobutyl, N-mono- or N,N-di(lower alkyl)-amino-lower alkyl, typically 3-(N,N-dimethylamino)propyl, amino, N-mono- or N,N-di-lower alkylamino and N-mono- or N,N-di-(hydroxy-lower alkyl) amino; disubstituted amino in aminocarbamoyl is also a 5 or 6-membered, saturated or unsaturated heterocyclyl with a bonding nitrogen atom and 0 to 2, especially 0 or 1, other heteroatoms selected from oxygen, nitrogen, and sulfur, which is unsubstituted or substituted, especially by one or two radicals from the group comprising lower alkyl, typically methyl, and also oxo. Preferred here is pyrrolidino (1-pyrrolidinyl), piperidino (1-piperidinyl), piperazino (1-piperazinyl), 4-lower al-kylpiperazino, typically 4-methylpiperazino, imidazolino (1-imidazolyl), morpholino (4-morpholinyl), or also thiomorpholino, S-oxo-thiomorpholino, or S,S-dioxothiomorpholino.

An acyl derived from an organic sulfonic acid, which is designated $Ac^2$, is especially one with the subformula $R^o$—$SO_2$—, wherein $R^o$ is a hydrocarbyl as defined above in the general and specific meanings, the latter also being generally preferred here. Especially preferred is lower alkylphenylsulfonyl, especially 4-toluenesulfonyl.

An acyl derived from a phosphoric acid, esterified if necessary, which is designated $Ac^3$, is especially one with the subformula $R^oO(R^oO)P(=O)$—, wherein the radicals $R^o$ are, independently of one another, as defined in the general and specific meanings indicated above.

Reduced data on substituents given hereinbefore and hereinafter are considered to be preferences.

Preferred compounds according to the invention are, for example, those wherein $R^0$ has the following preferred meanings: lower alkyl, especially methyl or ethyl, amino-lower alkyl, wherein the amino group is unprotected or is protected by a conventional amino protecting group—especially by lower alkoxycarbonyl, typically tert-lower alkoxycarbonyl, for example tert-butoxycarbonyl—e.g. aminomethyl, R,S—, R— or preferably S-1-aminoethyl, tert-butoxycarbonylaminomethyl or R, S—, R—, or preferably S-1-(tert-butoxycarbonylamino)ethyl, carboxy-lower alkyl, typically 2-carboxyethyl, lower alkoxycarbonyl-lower alkyl, typically 2-(tert-butoxycarbonyl)ethyl, cyano-lower alkyl, typically 2-cyanoethyl, tetrahydropyranyloxy-lower alkyl, typically 4-(tetrahydropyranyl)-oxymethyl, morpholino-lower alkyl, typically 2-(morpholino)ethyl, phenyl, lower alkylphenyl, typically 4-methylphenyl, lower alkoxyphenyl, typically 4-methoxyphenyl, imidazolyl-lower alkoxyphenyl, typically 4-[2-(imidazol-1-yl)ethyl)oxyphenyl, carboxyphenyl, typically 4-carboxyphenyl, lower alkoxycarbonylphenyl, typically 4-ethoxycarbonylphenyl or 4-methoxyphenyl, halogen-lower alkylphenyl, typically 4-chloromethylphenyl, pyrrolidinophenyl, typically 4-pyrrolidinophenyl, imidazol-1-ylphenyl, typically 4-(imidazolyl-1-yl)phenyl, piperazinophenyl, typically 4-piperazinophenyl, (4-lower alkylpiperazino)phenyl, typically 4-(4-methylpiperazino)phenyl, morpholinophenyl, typically 4-morpholinophenyl, pyrrolidino-lower alkylphenyl, typically 4-pyrrolidinomethylphenyl, imidazol-1-yl-lower alkylphenyl, typically 4-(imidazolyl-1-ylmethyl)phenyl, piperazino-lower alkylphenyl, typically 4-piperazinomethylphenyl, (4-lower alkylpiperazinomethyl)-phenyl, typically 4-(4-methylpiperazinomethyl) phenyl, morpholino-lower alkylphenyl, typically 4-morpholinomethylphenyl, piperazinocarbonylphenyl, typically 4-piperazinocarbonylphenyl, or (4-lower alkyl-piperazino) phenyl, typically 4-(4-methylpiperazino)phenyl.

Preferred acyl radicals $Ac^1$ are acyl radicals of a carboxylic acid which are characterised by the subformula $R^o$—CO—, wherein $R^o$ has one of the above general and preferred meanings of the hydrocarbyl radical $R^o$. Especially preferred radicals $R^o$ here are lower alkyl, especially methyl or ethyl, amino-lower alkyl, wherein the amino group is unprotected or protected by a conventional amino protecting group, especially by lower alkoxycarbonyl, typically tert-lower alkoxycarbonyl, for example tert-butoxycarbonyl, e.g. aminomethyl, R, S—, R—, or preferably S-1-aminoethyl, tert-butoxycarbonylaminomethyl or R, S—, R—, or preferably S-1-(tert-butoxycarbonylamino)ethyl, carboxy-lower alkyl, typically 2-carboxyethyl, lower alkoxycarbonyl-lower alkyl, typically 2-(tert-butoxycarbonyl)ethyl, tetrahydropyranyloxy-lower alkyl, typically 4-(tetrahydropyranyl)oxymethyl, phenyl, imidazolyl-lower alkoxyphenyl, typically 4-[2-(imidazol-1-yl)ethyl]oyxphenyl, carboxyphenyl, typically 4-carboxyphenyl, lower alkoxycarbonylphenyl, typically 4-ethoxycarbonylphenyl, halogen-lower alkylphenyl, typically 4-chloromethylphenyl, imidazol-1-ylphenyl, typically 4-(imidazolyl-1-yl)phenyl, pyrrolidino-lower alkylphenyl, typically 4-pyrrolidinomethylphenyl, piperazino-lower alkylphenyl, typically 4-piperazinomethylphenyl, (4-lower alkylpiperazinomethyl)phenyl, typically 4-(4-methyl-piperazinomethyl)phenyl, morpholino-lower alkylphenyl, typically 4-morpholinomethylphenyl, piperazinocarbonylphenyl, typically 4-piperazinocarbonylphenyl, or (4-lower alkylpiperazino)-phenyl, typically 4-(4-methylpiperazino)phenyl.

A further preferred Acyl $Ac^1$ is derived from monoesters of carbonic acid and is characterised by the subformula $R^o$—O—CO—. The lower alkyl radicals, especially tert-butyl, are especially preferred hydrocarbyl radicals $R^o$ in these derivatives.

Another preferred Acyl $Ac^1$ is derived from amides of carbonic acid (or also thiocarbonic acid) and is characterised by the formula $R^oHN$—C(=W)— or $R^oR^oN$—C(=W)—, wherein the radicals $R^o$ are, independently of one another, as defined above and W is sulfur and especially oxygen. In particular, compounds are preferred wherein $Ac^1$ is a radical of formula $R^oHN$—C(=W)—, wherein W is oxygen and $R^o$ has one of the following preferred meanings: morpholino-lower alkyl, typically 2-morpholinoethyl, phenyl, lower alkoxyphenyl, typically 4-methoxyphenyl or 4-ethoxyphenyl, carboxyphenyl, typically 4-carboxyphenyl, or lower alkoxy-carbonylphenyl, typically 4-ethoxycarbonylphenyl.

A preferred acyl $Ac^2$ of subformula $R^o$—$SO_2$—, wherein $R^o$ is a hydrocarbyl as defined in the above general and specific meanings, is lower alkylphenylsulfonyl, typically 4-toluenesulfonyl.

If p is 0, the nitrogen atom bonding $R_3$ is uncharged. If p is 1, then $R_4$ must also be present, and the nitrogen atom bonding $R_3$ and $R_4$ (quaternary nitrogen) is then positively charged.

The definitions for an aliphatic, carbocyclic, or carbocyclic-aliphatic radical with up to 29 carbon atoms each, or for a heterocyclic or heterocyclic-aliphatic radical with up to 20 carbon atoms each and up to 9 heteroatoms each, or acyl with up to 30 carbon atoms each, preferably match the definitions given for the corresponding radicals $R_3$ and $R_4$. Especially preferred is $R_5$ lower alkyl, especially methyl, or most especially hydrogen.

Z is especially lower alkyl, most especially methyl or hydrogen.

If the two bonds indicated by wavy lines are missing in ring A, then no double bonds (tetra-hydrogenated derivatives) are present between the carbon atoms characterised in formula I by the numbers 1, 2, 3, and 4, but only single bonds, whereas ring B is aromatic (double bonds between the carbon atoms characterised in formula I by 8 and 9 and those characterised by 10 and 11). If the two bonds indicated by wavy lines are missing in ring B, then no double bonds (tetra-hydrogenated derivatives) are present between the carbon atoms characterised in formula I by the numbers 8, 9, 10, and 11, but only single bonds, whereas ring A is aromatic (double bonds between the carbon atoms characterised in formula I by 1 and 2 and those characterised by 3 and 4). If the total of four bonds indicated by wavy lines are missing in rings A and B, and are replaced by a total of 8 hydrogen atoms, then no double bonds (octa-hydrogenated derivatives) are present between the carbon atoms numbered 1, 2, 3, 4, 8, 9, 10, and 11 in formula 1, but only single bonds.

By their nature, the compounds of the invention may also be present in the form of pharmaceutically, i.e. physiologically, acceptable salts, provided they contain salt-forming groups. For isolation and purification, pharmaceutically unacceptable salts may also be used. For therapeutic use, only pharmaceutically acceptable salts are used, and these salts are preferred.

Thus, compounds of formula I having free acid groups, for example a free sulfa, phosphoryl or carboxyl group, may exist as a salt, preferably as a physiologically acceptable salt with a salt-forming basic component. These may be primarily metal or ammonium salts, such as alkali metal or alkaline earth metal salts, for example sodium, potassium, magnesium or calcium salts, or ammonium salts with ammonia or suitable organic amines, especially tertiary monoamines and heterocyclic bases, for example triethylamine, tri-(2-hydroxyethyl)-amine, N-ethylpiperidine or N,N'-dimethylpiperazine.

Compounds of the invention having a basic character may also exist as addition salts, especially as acid addition salts with inorganic and organic acids, but also as quaternary salts. Thus, for example, compounds which have a basic group, such as an amino group, as a substituent may form acid addition salts with common acids. Suitable acids are, for example, hydrohalic acids, e.g. hydrochloric and hydrobromic acid, sulfuric acid, phosphoric acid, nitric acid or perchloric acid, or aliphatic, alicyclic, aromatic or heterocyclic carboxylic or sulfonic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, sallcylic, p-aminosalicylic acid, pamoic acid, methanesulfonic, ethanesulfonic, hydroxyethanesulfonic, ethylenedisulfonic, halobenzenesulfonic, toluenesulfonic, naphthalenesulfonic acids or sulfanilic acid, and also methionine, tryptophan, lysine or arginine, as well as ascorbic acid.

In view of the close relationship between the compounds (especially of formula I) in free form and in the form of their salts, including those salts that can be used as intermediates, for example in the purification or identification of the novel compounds, and of their solvates, any reference hereinbefore and hereinafter to the free compounds is to be understood as referring also to the corresponding salts, and the solvates thereof, for example hydrates, as appropriate and expedient.

The compounds of formula A, B, C, D, I, II, III, IV, V or VI especially those wherein $R_5$ is hydrogen, possess valuable pharmacological properties.

In the case of the groups of radicals or compounds mentioned hereinbefore and hereinafter, general definitions may, insofar as appropriate and expedient, be replaced by the more specific definitions stated hereinbefore and hereinafter.

Preference is given to a compounds of formula I, II, III, IV, V, VI wherein $R_1$ and $R_2$ independently of each other are lower alkyl, lower alkyl substituted by halogen, $C_6$-$C_{14}$aryl, hydroxy, lower alkoxy, phenyl-lower alkoxy, phenyloxy, lower alkanoyloxy, benzoyloxy, amino, lower alkylamino, lower alkanoylamino, phenyl-lower alkylamino, N,N-di-lower alkylamino, N,N-di-(phenyl-lower alkyl)amino, cyano, mercapto, lower alkylthio, carboxy, lower alkoxycarbonyl, carbamoyl, N-lower alkylcarbamoyl, N,N-di-lower alkyl-carbamoyl, sulfo, lower alkanesulfonyl, lower alkoxysulfonyl, aminosulfonyl, N-lower-alkylaminosulfonyl or N,N-di-lower alkylaminosulfonyl; halogen; lower alkoxy; $C_6$-$C_{14}$aryloxy; $C_6$-$C_{14}$aryl-lower alkoxy; lower alkanoyloxy; $C_6$-$C_{14}$arylcarbonyloxy; amino monosubstituted or disubstituted by lower alkyl, $C_6$-$C_{14}$aryl, $C_6$-$C_{14}$aryl-lower alkyl, lower alkanoyl or $C_6$-$C_{12}$aryl-carbonyl; cyano; nitro; mercapto; lower alkylthio; $C_6$-$C_{14}$arylthio; $C_6$-$C_{14}$aryl-lower alkylthio; lower alkanoylthio; $C_6C_{14}$aryl-lower alkanoylthio; carboxy; lower alkoxycarbonyl, $C_6$-$C_{14}$aryl-lower alkoxycarbonyl; $C_6$-$C_{14}$aryloxycarbonyl; carbamoyl; carbamoyl N-mono- or N,N-disubstituted by lower alkyl, $C_6$-$C_{14}$aryl or $C_6$-$C_{14}$aryl-lower alkyl; sulfo; $C_6$-$C_{14}$arylsulfonyl; $C_6$-$C_{14}$aryl-lower alkanesulfonyl; lower alkanesulfonyl; or aminosulfonyl N-mono- or N,N-disubstituted by lower alkyl, $C_6$-$C_{14}$aryl or $C_6$-$C_{14}$aryl-lower alkyl, wherein $C_6$-$C_{14}$aryl is an aryl radical with 6 to 12 carbon atoms in the ring system, which may be unsubstituted or substituted by halogen, phenyl or naphthyl, hydroxy, lower alkoxy, phenyl-lower alkoxy, phenyloxy, lower alkanoyloxy, benzoyloxy, amino, lower alkylamino, lower alkanoylamino, phenyl-lower alkylamino, N,N-di-lower alkylamino, N,N-di-(phenyl-lower alkyl) amino, cyano, mercapto, lower alkylthio, carboxy, lower alkoxycarbonyl, carbamoyl, N-lower alkyl-carbamoyl, N,N-di-lower alkylcarbamoyl, sulfo, lower alkanesulfonyl, lower alkoxysulfonyl, aminosulfonyl, N-lower alkylaminosulfonyl or N,N-di-lower alkylaminosulfonyl;

n and m are independently of each other 0 or 1 or 2, preferably 0;

$R_3$, $R_4$, $R_8$, $R_{10}$ are independently of each other hydrogen, lower alkyl, lower alkenyl or lower alkadienyl, which are each unsubstituted or monosubstituted or polysubstituted, preferably monosubstituted or disubstituted by a substituent independently selected from lower alkyl; hydroxy; lower alkoxy, which may be unsubstituted or mono-, di-, or trisubstituted by (i) heterocyclyl with 4 to 12 ring atoms, which may be unsaturated, wholly saturated, or partly saturated, is monocyclic or bicyclic and may contain up to three heteroatoms selected from nitrogen, oxygen and sulfur, and is most especially pyrrolyl, for example 2-pyrrolyl or 3-pyrrolyl, pyridyl, for example 2-, 3- or 4-pyridyl, or in a broader sense also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; Imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl, (ii) by halogen, (iii) by hydroxy or (iv) by lower alkoxy; phenoxy; phenyl-lower alkoxy; heterocyclyoxy, wherein heterocyclyl is pyrrolyl, for example 2-pyrrolyl or 3-pyrrolyl, pyridyl, for example 2-, 3- or 4-pyridyl, or in a broader sense also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl, such as especially 2- or 4-tetrahydropyranyloxy; lower alkanoyloxy; carboxy; lower alkoxycarbonyl; phenyl-lower alkoxycarbonyl; mercapto; lower alkylthio; phenylthio; halogen; halogen-lower alkyl; oxo (except in the 1-position, because otherwise acyl); azido; nitro; cyano; amino; mono-lower alkylamino; di-lower alkylamino; pyrrolidino; imidazol-1-yl; piperidino; piperazino; 4-lower alkylpiperazino; morpholino; thiomorpholino; diphenylamino or dibenzylamino unsubstituted or substituted in the phenyl part by lower alkyl, lower alkoxy, halogen and/or nitro; lower alkoxycarbonylamino; phenyl-lower alkoxycarbonylamino unsubstituted or substituted in the phenyl part by lower alkyl or lower alkoxy; fluorenylmethoxycarbonylamino; amino-lower alkyl; monosubstituted or disubstituted amino-lower alkyl, wherein the amino substituent is selected from lower alkyl, hydroxy-lower alkyl, $C_3$-$C_8$cycloalkyl, amino-lower alkyl, N-mono- or N,N-di(-lower alkyl)amino-lower alkyl, amino, N-mono- or N,N-di-lower alkylamino and N-mono- or N,N-di-(hydroxy-lower alkyl)amino; pyrrolidino-lower alkyl; piperidino-lower alkyl; piperazino-lower alkyl; 4-lower alkylpiperazino-lower alkyl; imidazol-1-yl-lower alkyl; morpholino-lower alkyl; thiomorpholino-lower alkyl; S-oxo-thiomorpholino-lower alkyl; S,S-dioxothiomorpholino-lower alkyl; lower alkylendioxy; sulfamoyl; sulfo; carbamoyl; ureido; guanidino; cyano; aminocarbonyl (carbamoyl) and aminocarbonyloxy, which are substituted by one or two radicals on the nitrogen, wherein the amino substituents are selected independently of one another from the group comprising lower alkyl, hydroxy-lower alkyl, $C_3$-$C_8$cycloalkyl, amino-lower alkyl, N-mono- or N,N-di(-lower alkyl)amino-lower alkyl, amino, N-mono- or N,N-di-lower alkylamino and N-mono- or N,N-di-(hydroxy-lower alkyl)amino; pyrrolidinocarbonyl; piperidinocarbonyl; piperazinocarbonyl; 4-lower alkylpiperazinocarbonyl; imidazolinocarbonyl; morpholinocarbonyl; thiomorpholinocarbonyl; S-oxo-thiomorpholinocarbonyl; and S,S-dioxothiomorpholino;

phenyl, naphthyl, phenyl-lower alkyl or phenyl-lower alkenyl with a terminal phenyl radical, which is unsubstituted or monosubstituted or disubstituted by the radicals named above as substituents of lower alkyl, lower alkenyl or lower alkadienyl;

or heterocyclyl-lower alkyl, wherein heterocyclyl is pyrrolyl, for example 2-pyrrolyl or 3-pyrrolyl, pyridyl, for example 2-, 3- or 4-pyridyl, or in a broader sense also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl, which in each case are unsubstituted or monosubstituted or disubstituted by the radicals named above as substituents of lower alkyl, lower alkenyl, or lower alkadienyl;

or acyl of the subformula Y—C(=W)—, wherein W is oxygen and Y is hydrogen, $R^\circ$, $R^\circ$—O—, $R^\circ$HN—, or $R^\circ R^\circ$N— (wherein the radicals $R^\circ$ may be the same or different), or acyl of the subformula R—$SO_2$—, whereby $R_4$ may also be absent for the compound of formula II;

or $R_4$ is absent for compounds of formula II, hydrogen or $CH_3$ for compounds of formula I, and $R_3$ is acyl of the subformula Y—C(=W)—, wherein W is oxygen and Y is hydrogen, $R^\circ$, $R^\circ$—O—, $R^\circ$HN—, or $R^\circ R^\circ$N— (wherein the radicals $R^\circ$ may be the same or different), or is acyl of the subformula $R^\circ$—$SO_2$—, wherein $R^\circ$ in the said radicals has the following meanings: substituted or unsubstituted lower alkyl, especially methyl or ethyl, amino-lower alkyl hydroxy-lower alkyl, wherein the amino group is unprotected or is protected by a conventional amino protecting group—especially by lower alkoxycarbonyl, typically tert-lower alkoxycarbonyl, for example tert-butoxycarbonyl—e.g. aminomethyl, R, S—, R— or preferably S-1-aminoethyl, tert-butoxycarbonylaminomethyl or R, S—, R—, or preferably S-1-(tert-butoxycarbonylamino) ethyl, carboxy-lower alkyl, typically 2-carboxyethyl, lower alkoxycarbonyl-lower alkyl, typically 2-(tert-butoxycarbonyl)ethyl, cyano-lower alkyl, typically 2-cyanoethyl, tetrahydropyranyloxy-lower alkyl, typically 4-(tetrahydropyranyl) oxymethyl, morpholino-lower alkyl, typically 2-(morpholino)ethyl, phenyl, lower alkylphenyl, typically 4-methylphenyl, lower alkoxyphenyl, typically 4-methoxyphenyl, imidazolyl-lower alkoxyphenyl, typically 4-[2-(imidazol-1-yl)ethyl)oxyphenyl, carboxyphenyl, typically 4-carboxyphenyl, lower alkoxycarbonylphenyl, typically 4-ethoxycarbonylphenyl or 4-methoxyphenyl, halogen-lower alkylphenyl, typically 4-chloromethylphenyl, pyrrolidinophenyl, typically 4-pyrrolidinophenyl, imidazol-1-ylphenyl, typically 4-(imidazolyl-1-yl)phenyl, piperazinophenyl, typically 4-piperazinophenyl, (4-lower alkylpiperazino)phenyl, typically 4-(4-methylpiperazino) phenyl, morpholinophenyl, typically 4-morpholinophenyl, pyrrolidino-lower alkylphenyl, typically 4-pyrrolidinomethylphenyl, imidazol-1-yl-lower alkylphenyl, typically 4-(imidazolyl-1-ylmethyl)phenyl, piperazino-lower alkylphenyl, typically 4-piperazinomethylphenyl, (4-lower alkylpiperazinomethyl)-phenyl, typically 4-(4-methylpiperazinomethyl) phenyl, morpholino-lower alkylphenyl, typically 4-morpholinomethylphenyl, piperazinocarbonylphenyl, typically 4-piperazinocarbonylphenyl, or (4-lower alkylpiperazino) phenyl, typically 4-(4-methylpiperazino)phenyl.

p is 0 if $R_4$ is absent, or is 1 if $R_3$ and $R_4$ are both present and in each case are one of the aforementioned radicals (for compounds of formula II);

$R_5$ is hydrogen or lower alkyl, especially hydrogen,

X stands for 2 hydrogen atoms, for O, or for 1 hydrogen atom and hydroxy; or for 1 hydrogen atom and lower alkoxy;

Z is hydrogen or especially lower alkyl, most especially methyl;

and for compounds for formula II, either the two bonds characterised by wavy lines are preferably absent in ring A and replaced by 4 hydrogen atoms, and the two wavy lines in ring B each, together with the respective parallel bond, signify a double bond;

or also the two bonds characterised by wavy lines are absent in ring B and replaced by a total of 4 hydrogen atoms, and the two wavy lines in ring A each, together with the respective parallel bond, signify a double bond;

or both in ring A and in ring B all of the 4 wavy bonds are absent and are replaced by a total of 8 hydrogen atoms;

or a salt thereof, if at least one salt-forming group is present.

Particular preference is given to a compound of formula I wherein;

m and n are each 0;

$R_3$ and $R_4$ are independently of each other hydrogen, lower alkyl unsubstituted or mono- or disubstituted, especially monosubstituted, by radicals selected independently of one another from carboxy; lower alkoxycarbonyl; and cyano;

or $R_4$ is hydrogen or —$CH_3$, and $R_3$ is as defined above or preferably $R_3$ is, acyl of the subformula $R^o$—CO, wherein $R^o$ is lower alkyl; amino-lower alkyl, wherein the amino group is present in unprotected form or is protected by lower alkoxycarbonyl; tetrahydropyranyloxy-lower alkyl; phenyl; imidazolyl-lower alkoxyphenyl; carboxyphenyl; lower alkoxycarbonylphenyl; halogen-lower alkylphenyl; imidazol-1-ylphenyl; pyrrolidino-lower alkylphenyl; piperazino-lower alkylphenyl; (4-lower alkylpiperazinomethyl)phenyl; morpholino-lower alkylphenyl; piperazinocarbonylphenyl; or (4-tower alkylpiperazino)phenyl;

or is acyl of the subformula $R^o$—O—CO—, wherein $R^o$ is lower alkyl;

or is acyl of the subformula $R^o$HN—C(=W)—, wherein W is oxygen and $R^o$ has the following meanings: morpholino-lower alkyl, phenyl, lower alkoxyphenyl, carboxyphenyl, or lower alkoxycarbonylphenyl;

or $R_3$ is lower alkylphenylsulfonyl, typically 4-toluenesulfonyl;

further specific examples of preferred $R_3$ groups are described below for the preferred compounds of formula II, $R_5$ is hydrogen or lower alkyl, especially hydrogen, X stands for 2 hydrogen atoms or for O;

Z is methyl or hydrogen;

or a salt thereof, if at least one salt-forming group is present.

Particular preference is given to a compound of formula II wherein m and n are each 0;

$R_3$ and $R_4$ are independently of each other hydrogen, lower alkyl unsubstituted or mono- or disubstituted, especially monosubstituted, by radicals selected independently of one another from carboxy; lower alkoxycarbonyl; and cyano;

whereby $R_4$ may also be absent;

or $R_4$ is absent, and $R_3$ is acyl from the subformula $R^o$—CO, wherein $R^o$ is lower alkyl, especially methyl or ethyl; amino-lower alkyl, wherein the amino group is unprotected or protected by lower alkoxy-carbonyl, typically tert-lower alkoxycarbonyl, for example tert-butoxycarbonyl, e.g. aminomethyl, R, S—, R—, or preferably S-1-aminoethyl, tert-butoxycarbonylaminomethyl or R, S—, R—, or preferably S-1-(tert-butoxycarbonylamino)ethyl; tetrahydropyranyloxy-lower alkyl, typically 4-(tetrahydropyranyl)oxymethyl; phenyl; imidazolyl-lower alkoxyphenyl, typically 4-[2-(imidazol-1-yl)ethyl) oyxphenyl; carboxyphenyl, typically 4-carboxyphenyl; lower alkoxycarbonylphenyl, typically 4-methoxy- or 4-ethoxycarbonylphenyl; halogen-lower alkylphenyl, typically 4-chloromethylphenyl; imidazol-1-ylphenyl, typically 4-(imidazolyl-1-yl)-phenyl; pyrrolidino-lower alkylphenyl, typically 4-pyrrolidinomethylphenyl; piperazino-lower alkylphenyl, typically 4-piperazinomethylphenyl; (4-lower alkylpiperazinomethyl)phenyl, typically 4-(4-methylpiperazinomethyl)phenyl; morpholino-lower alkylphenyl, typically 4-morpholinomethylphenyl; piperazinocarbonylphenyl, typically 4-piperazinocarbonylphenyl; or (4-lower alkylpiperazino)phenyl, typically 4-(4-methylpiperazino)phenyl;

or is acyl of the subformula $R^o$—O—CO—, wherein $R^o$ is lower alkyl;

or is acyl of the subformula $R^o$HN—C(=W)—, wherein W is oxygen and $R^o$ has the following preferred meanings: morpholino-lower alkyl, typically 2-morpholinoethyl, phenyl, lower alkoxyphenyl, typically 4-methoxyphenyl or 4-ethoxyphenyl, carboxyphenyl, typically 4-carboxyphenyl, or lower alkoxycarbonylphenyl, typically 4-ethoxycarbonylphenyl;

or is lower alkylphenylsulfonyl, typically 4-toluenesulfonyl;

p is 0 if $R_4$ is absent, or is 1 if $R_3$ and $R_4$ are both present and in each case are one of the aforementioned radicals;

$R_5$ is hydrogen or lower alkyl, especially hydrogen,

X stands for 2 hydrogen atoms or for O;

Z is methyl or hydrogen;

and either the two bonds characterised by wavy lines are preferably absent in ring A and replaced by 4 hydrogen atoms, and the two wavy lines in ring B each, together with the respective parallel bond, signify a double bond;

or also the two bonds characterised by wavy lines are absent in ring B and replaced by a total of 4 hydrogen atoms, and the two wavy lines in ring A each, together with the respective parallel bond, signify a double bond;

or both in ring A and in ring B all of the 4 wavy bonds are absent and are replaced by a total of 8 hydrogen atoms;

or a salt thereof, if at least one salt-forming group is present.

Most especially preferred compounds of formula II are selected from;

8,9,10,11-Tetrahydrostaurosporine;

N-[4-(4-methylpiperaziN-1-ylmethyl)benzoyl]-1,2,3,4-tetrahydrostaurosporine;

N-(4-chloromethylbenzoyl)-1,2,3,4-tetrahydrostaurosporine;

N-(4-(pyrrolidin-1-ylmethyl)benzoyl)-1,2,3,4-tetrahydrostaurosporine;

N-(4-(morpholin-4-ylmethyl)benzoyl)-1,2,3,4-tetrahydrostaurosporine;

N-(4-(piperazin-1-ylmethyl)benzoyl)-1,2,3,4-tetrahydrostaurosporine;

N-ethyl-1,2,3,4-tetrahydrostaurosporine;

N-tosyl-1,2,3,4-tetrahydrostaurosporine;

N-triflouroacetyl-1,2,3,4-tetrahydrostaurosporine;

N-[4-(2-imidazol-1-yl-ethoxy)benzoyl]-1,2,3,4-tetrahydrostaurosporine;

N-methoxycarbonylmethyl-1,2,3,4-tetrahydrostaurosporine;

N-carboxymethyl-1,2,3,4-tetrahydrostaurosporine;

N-terephthaloylmethyl ester-1,2,3,4-tetrahydrostaurosporine;

N-terephthaloyl-1,2,3,4-tetrahydrostaurosporine;

N-(4-ethylpiperazinylcarbonylbenzoyl)-1,2,3,4-tetrahydrostaurosporine;

N-(2-cyanoethyl)-1,2,3,4-tetrahydrostaurosporine;

N-benzoyl-1,2,3,4-tetrahydrostaurosporine;

N,N-dimethyl-1,2,3,4-tetrahydrostaurosporinium iodide;

N-BOC-glycyl-1,2,3,4-tetrahydrostaurosporine;

N-glycyl-1,2,3,4-tetrahydrostaurosporine;

N-(3-(tert-butoxycarbonyl)propyl)-1,2,3,4-tetrahydrostaurosporine;

N-(3-carboxypropyl)-1,2,3,4-tetrahydrostaurosporine;

N-(4-imidazol-1-yl)benzoyl]-1,2,3,4-tetrahydrostaurosporine;

N-[(tetrahydro-2h-pyran-4-yloxy)acetyl]-1,2,3,4-tetrahydrostaurosporine;

N-BOC-I-alanyl-1,2,3,4-tetrahydrostaurosporine;

N-I-alanyl-1,2,3,4-tetrahydrostaurosporine hydrochloride;

N-methyl-1,2,3,4-tetrahydro-6-methylstaurosporine;

N-(4-carboxyphenylaminocarbonyl)-1,2,3,4-tetrahydrostaurosporine;

N-(4-ethylphenylaminocarbonyl)-1,2,3,4-tetrahydrostaurosporine;

N-(N-phenylaminocarbonyl)-1,2,3,4-tetrahydrostaurosporine;

N-(N-[2-(1-morpholino)ethyl]aminocarbonyl)-1,2,3,4-tetrahydrostaurosporine;

N-(N-[4-methoxyphenyl]aminocarbonyl)-1,2,3,4-tetrahydrostaurosporine;

1,2,3,4-tetrahydro-6-methylstaurosporine;

N-BOC-1,2,3,4-tetrahydrostaurosporine;

N-BOC-1,2,3,4-tetrahydro-6-methylstaurosporine;

N-BOC-1,2,3,4-tetrahydro-6-methyl-7-oxo-staurosporine;

1,2,3,4,8,9,10,11-octahydrostaurosporine;

or a pharmaceutically acceptable salt thereof, if at least one salt-forming group is present.

Most especially preferred is the compound of formula I designated 1,2,3,4-tetrahydrostaurosporine, or a (particularly pharmaceutically acceptable) salt thereof (here, m und n in formula I are 0, $R_3$ is hydrogen, $R_4$ is absent, provided no salt is present (p=0), or is hydrogen if a salt is present (p=1), $R_5$ is hydrogen, the two bonds represented by wavy lines are absent in Ring A and are replaced by a total of 4 hydrogen atoms and the two bonds represented by wavy lines in Ring B are in each case a double bond together with the parallel bonds, X stands for 2 hydrogen atoms, and Z is methyl).

Most especially preferred are the compounds of formula A wherein;

A) X=O; $R_1$, $R_2$, $R_5$=H; Q=—$(CH_2)_2$—O—CH($CH_2$)OH—$(CH_2)_2$—

B) X=O; $R_1$, $R_2$, $R_5$=H; Q=—$(CH_2)_2$—O—CH($CH_2$N($CH_3$)$_2$)—$(CH_2)_2$—

C) X=2 hydrogen atoms; $R_1$, $R_2$, $R_5$=H;

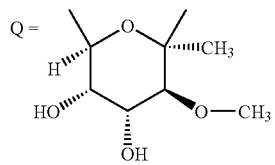

Most especially preferred are the compounds of formula I wherein;

A) X=2 hydrogen atoms; $R_1$, $R_2$, $R_3$, $R_5$=H; $R_4$=$CH_3$; Z=$CH_3$ (staurosporine)

B) X=1 hydrogen and 1 hydroxy atoms in (R) or (S) isomeric form; $R_1$, $R_2$, $R_3$, $R_5$=H; $R_4$=$CH_3$; Z=$CH_3$ (UCN-01 and UCN-02)

C) X=2 hydrogen atoms; $R_1$, $R_2$, $R_5$=H; $R_4$=$CH_3$; $R_3$=benzoyl; Z=$CH_3$ (CGP41251 or PKC412 or MIDOSTAURIN)

D) X=O; $R_1$, $R_2$, $R_5$=H; $R_3$=$CH_3$; $R_4$=ethyloxycarbonyl; Z=$CH_3$ (NA 382; CAS=143086-33-3)

E) X=1 hydrogen and 1 hydroxy atom; $R_1$, $R_2$, $R_5$=H; $R_3$=$CH_3$; Z=$CH_3$; and $R_4$ is selected from —$(CH_2)_2$OH; —$CH_2CH(OH)CH_2OH$; —CO($CH_2$)$_2$$CO_2$Na; —$(CH_2)_3CO_2H$; —$COCH_2N(CH_3)_2$;

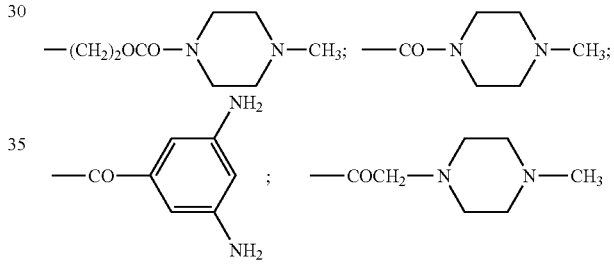

F) X=2 hydrogen atoms; $R_1$, $R_2$, $R_5$=H; $R_3$=$CH_3$; Z=$CH_3$; and $R_4$ is selected from N-[0-(tetrahydropyran-4-yl)-D-lactoyl]; N-[2-methyl-2-(tetrahydropyran-4-yloxy)-propionyl; N-[0-(tetrahydropyran-4-yl)-L-lactoyl]; N-[0-(tetrahydropyran-4-yl)-D-lactoyl]; N-[2-(tetrahydro-pyran-4-yloxy)-acetyl)]

G) X=O; $R_1$, $R_2$, $R_5$=H; $R_3$=$CH_3$; Z=$CH_3$; and $R_4$ is selected from N-[0-(tetrahydropyran-4-yl)-D-lactoyl]; N-[2-(tetrahydro-pyran4-yloxy)-acetyl)]

H) X=1 hydrogen and 1 hydroxy atom; $R_1$, $R_2$, $R_5$=H; $R_3$=$CH_3$; Z=$CH_3$; and $R_4$ is selected from N-[0-(tetrahydropyran-4-yl)-D-lactoyl]; N-[2-(tetrahydro-pyran-4-yloxy)-acetyl)]

The abbreviation "CAS" means the CHEMICAL ABSTRACTS registry number.

The most preferred compounds of formula I e.g. MIDOSTAURIN [International Nonproprietary Name] are covered and have been specifically described by the European patent No. 0 296 110 published on Dec. 21, 1988, as well as in U.S. Pat. No. 5,093,330 published on Mar. 3, 1992, and Japanese Patent No. 2 708 047. Other preferred compounds are covered and described by the patent applications WO 95/32974 and WO 95/32976 both published on Dec. 7, 1995. All the compounds described in these documents are incorporated into the present application by reference.

Most especially preferred are the compounds of formula III wherein;
A) X=2 hydrogen atoms; $R_1$, $R_2$, $R_5$=H; $R_6$=CH$_3$; $R_7$=methyloxycarbonyl; Z=H (2-methyl K252a)
B) X=2 hydrogen atoms; $R_1$, $R_2$, $R_5$, $R_6$=H; $R_7$=methyloxycarbonyl; Z=H (K-252a)
C) X=2 hydrogen atoms; $R_1$, $R_2$, $R_5$, $R_6$=H; $R_7$=methyloxycarbonyl; Z=CH$_3$ (KT-5720)

Most especially preferred are the compounds of formula IV wherein;
A) X=O; $R_1$, $R_2$, $R_5$=H; $R_9$=CH$_2$—NMe$_2$; $R_6$=CH$_3$; m'=n'=2
B) X=O; $R_1$, $R_2$, $R_5$=H; $R_9$=CH$_2$—NH$_2$; $R_8$=CH$_3$; m'=2; n'=1 (Ro-31-8425; CAS=151342-35-7)

Most especially preferred are the compounds of formula V wherein;
A) X=O; $R_1$, $R_2$, $R_5$=H; $R_8$=CH$_3$; $R_{10}$=—(CH$_2$)$_3$—NH$_2$; (Ro-31-7549; CAS=138516-31)
B) X=O; $R_1$, $R_2$, $R_5$=H; $R_8$=CH$_3$; $R_{10}$=—(CH$_2$)$_3$—S—(C=NH)—NH$_2$; (Ro-31-8220; CAS=125314-64-9))
C) X=O; $R_1$, $R_2$, $R_5$=H; $R_8$=CH$_3$; $R_{10}$=—CH$_3$;

Most especially preferred are the compounds of formula VI wherein;
A) X=2 hydrogen atoms; $R_1$, $R_2$, $R_5$=H; $R_4$=CH$_3$; Z=CH$_3$; $R_3$ selected from methyl or (C$_1$-C$_{10}$)alkyl, arylmethyl, C$_6$H$_2$CH$_2$—

STAUROSPORINE DERIVATIVES and their manufacturing process have been specifically described in many prior documents, well known by the man skilled in the art.

Compounds of formula A, B, C, D and their manufacturing process have for instance, been described in the European patents No. 0 657 458 published on Jun. 14, 1995, in the European patents No. 0 624 586 published on Nov. 17, 1994, in the European patents No. 0 470 490 published on Feb. 12, 1992, in the European patents No. 0 328 026 published on Aug. 16, 1989, in the European patents No. 0 384 349 published on Aug. 29, 1990, as well as in many publications such as Barry M. Trost* and Weiping Tang Org. Lett., 3(21), 3409-3411.

Compounds of formula I and their manufacturing processes have specifically been described in the European patents No. 0 296 110 published on Dec. 21, 1988, as well as in U.S. Pat. No. 5,093,330 published on Mar. 3, 1992, and Japanese Patent No. 2 708 047. Compounds of formula I having a tetrahydropyran-4-yl)-lactoyl substitution on $R_4$ have been described in the European patent No. 0 624 590 published on Nov. 17, 1994. Other compounds have been described in the European patent No. 0 575 955 published Dec. 29, 1993, European patent No. 0 238 011 published on Sep. 23, 1987 (UCN-O1), International patent application EP98104141 published as WO99/02532 on Jul. 3, 1998.

Compounds of formula II and their manufacturing processes have specifically been described in the European patents No. 0 296 110 published on Dec. 21, 1988, as well as in U.S. Pat. No. 5,093,330 published on Mar. 3, 1992, and Japanese Patent No. 2 708 047.

Compounds of formula III and their manufacturing processes have specifically been described in the patent applications claiming the priority of the US patent application US 920102 filed on Jul. 24, 1992. (i.e. European patents No. 0 768 312 published on Apr. 16, 1997, No. 1 002 534 published May 24, 2000, No. 0 651 754 published on May 10, 1995).

Compounds of formula IV and their manufacturing processes have specifically been described in the patent applications claiming the priority of the British patent applications GB 9309602 and GB 9403249 respectively filed on May 10, 1993, and on Feb. 21, 1994. (i.e. European patents No. 0 624 586 published on Nov. 17, 1994, No. 1 002 534 published May 24, 2000, No. 0 651 754 published on May 10, 1995).

Compounds of formula V and their manufacturing processes have specifically been described in the patent applications claiming the priority of the British patent applications GB 8803048, GB 8827565, GB 8904161 and GB 8928210 respectively filed on Feb. 10, 1988, Nov. 25, 1988, Feb. 23, 1989 and Dec. 13, 1989. (i.e. European patents No. 0 328 026 published on Aug. 16, 1989, and No. 0 384 349 published Aug. 29, 1990).

Compounds of formula VI and their manufacturing processes have specifically been described in the patent applications claiming the priority of the U.S. patent applications Ser. No. 07/777,395 (Con), filed on Oct. 10, 1991 (i.e. International patent application WO 93/07153 published on Apr. 15, 1993).

In each case where citations of patent applications or scientific publications are given in particular for the STAUROSPORINE DERIVATIVE compounds, the subject-matter of the final products, the pharmaceutical preparations and the claims are hereby incorporated into the present application by reference to these publications.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The preferred STAUROSPORINE DERIVATIVE according to the invention is N-[(9S, 10R,11R,13R)-2,3,10,11,12, 13-hexahydro-10-methoxy-9-methyl-1-oxo-9,13-epoxy-1H, 9H-diindolo[1,2,3-gh:3',2',1'-lm]pyrrolo[3,4j][1,7] benzodiazonin-11-yl]-N-methylbenzamide of the formula (VII):

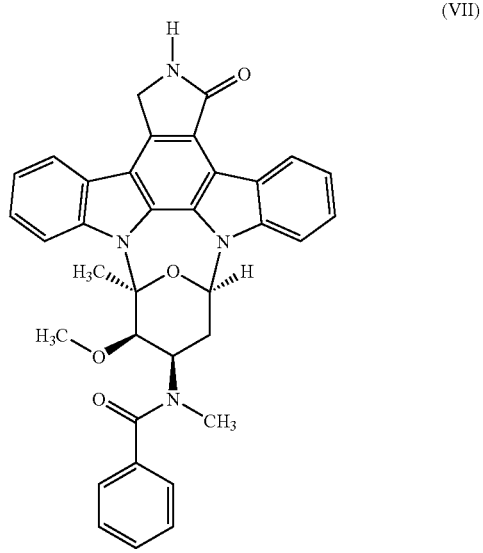 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4]

(VII)

or a salt thereof, (hereinafter: "Compound of formula VII or MIDOSTAURIN").

Compound of formula VII is also known as MIDOSTAURIN [International Nonproprietary Name] or PKC412.

MIDOSTAURIN is a derivative of the naturally occurring alkaloid staurosporine, and has been specifically described in the European patent No. 0 296 110 published on Dec. 21, 1988, as well as in U.S. Pat. No. 5,093,330 published on Mar. 3, 1992, and Japanese Patent No. 2 708 047.

It has now surprisingly been found that MIDOSTAURIN possesses therapeutic properties, which render it particularly useful for the treatment of allergic rhinitis, allergic dermatitis, drug allergy or food allergy, angioedema, urticaria, sudden infant death syndrome, bronchopulmonary aspergillosis, multiple sclerosis, or mastocytosis. Particularly surprising is that Midostaurin is also effective in the prevention or treatment of the diseases and conditions mentioned hereinbefore that have developed resistance against imatinib or a pharmaceutically acceptable salt thereof.

STAUROSPORINE DERIVATIVES e.g. MIDOSTAURIN were originally identified as inhibitor of protein kinase C (PKC) (Meyer T, Regenass U, Fabbro D, et al: Int J Cancer 43: 851-856, 1989).

The present invention thus concerns the use of STAUROSPORINE DERIVATIVES for the preparation of a drug for the treatment allergic rhinitis, allergic dermatitis, drug allergy or food allergy, angioedema, urticaria, sudden infant death syndrome, bronchopulmonary aspergillosis, multiple sclerosis, or mastocytosis. Further, the present invention concerns the use of STAUROSPORINE DERIVATIVES for the preparation of a drug for the treatment allergic rhinitis, allergic dermatitis, drug allergy or food allergy, angioedema, urticaria, sudden infant death syndrome, bronchopulmonary aspergillosis, multiple sclerosis, or mastocytosis with resistance to imatinib or a pharmaceutically acceptable salt thereof.

In another embodiment, the instant invention provides a method for treating allergic rhinitis, allergic dermatitis, drug allergy or food allergy, angioedema, urticaria, sudden infant death syndrome, bronchopulmonary aspergillosis, multiple sclerosis, or mastocytosis, all of these diseases and conditions also with resistance to imatinib or a pharmaceutically acceptable salt thereof, comprising administering to a mammal in need of such treatment a therapeutically effective amount of a STAUROSPORINE DERIVATIVE, a pharmaceutically acceptable salt or prodrug thereof.

Preferably the instant invention provides a method for treating mammals, especially humans, suffering from allergic rhinitis, allergic dermatitis, drug allergy or food allergy, angioedema, urticaria, sudden infant death syndrome, bronchopulmonay aspergillosis, multiple sclerosis, or mastocytosis comprising administering to a mammal in need of such treatment an therapeutically effective amount of N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-N-methylbenzamide of the formula (VII), or a pharmaceutically acceptable salt thereof.

The instant invention also concerns a method wherein the therapeutically effective amount of the compound of formula VII is administered to a mammal subject 7 to 4 times a week or about 100% to about 50% of the days in the time period, for a period of from one to six weeks, followed by a period of one to three weeks, wherein the agent is not administered and this cycle being repeated for from 1 to several cycles.

In another embodiment, the instant invention relates to the use of STAUROSPORINE DERIVATIVES for the preparation of a pharmaceutical composition for use in treating allergic rhinitis, allergic dermatitis, drug allergy or food allergy, angioedema, urticaria, sudden infant death syndrome, bronchopulmonary aspergillosis, multiple sclerosis, or mastocytosis, more particularly for treating allergic rhinitis, allergic dermatitis, drug allergy or food allergy, angioedema, urticaria, sudden infant death syndrome, bronchopulmonary aspergillosis, multiple sclerosis, or mastocytosis with resistance to imatinib.

In vivo, the activity of the STAUROSPORINE DERIVATIVES especially compounds of formula I or II, can be demonstrated, for example, in a single or up to three oral administrations per day to animals at doses in the range of 0.1 to 10 or 1 to 5 mg/kg of body weight per day.

Allergic rhinitis, allergic dermatitis, drug allergy or food allergy, angioedema, urticaria, sudden infant death syndrome, bronchopulmonary aspergillosis, multiple sclerosis, or mastocytosis may in some cases be treated with the tyrosine kinase inhibitor imatinib but frequently a relapse occurs and it was surprisingly found that the STAUROSPORINE DERIVATIVES and MIDOSTAURIN in particular are still active in these instances.

The precise dosage of STAUROSPORINE DERIVATIVES to be employed for treating the diseasesand conditions mentioned hereinbefore depends upon several factors including the host, the nature and the severity of the condition being treated, the mode of administration. However, in general, satisfactory results are achieved when the STAUROSPORINE DERIVATIVE is administered parenterally, e.g., intraperitoneally, intravenously, intramuscularly, subcutaneously, intratumorally, or rectally, or enterally, e.g., orally, preferably intravenously or, preferably orally, intravenously at a daily dosage of 0.1 to 10 mg/kg body weight, preferably 1 to 5 mg/kg body weight. In human trials a total dose of 225 mg/day was most presumably the Maximum Tolerated Dose (MTD). A preferred intravenous daily dosage is 0.1 to 10 mg/kg body weight or, for most larger primates, a daily dosage of 200-300 mg. A typical intravenous dosage is 3 to 5 mg/kg, three to five times a week.

Most preferably, the STAUROSPORINE DERIVATIVES, especially MIDOSTAURIN, are administered orally, by dosage forms such as microemulsions, soft gels or solid dispersions in dosages up to about 250 mg/day, in particular 225 mg/day, administered once, twice or three times daily.

Usually, a small dose is administered initially and the dosage is gradually increased until the optimal dosage for the host under treatment is determined. The upper limit of dosage is that imposed by side effects and can be determined by trial for the host being treated.

The STAUROSPORINE DERIVATIVES may be combined with one or more pharmaceutically acceptable carriers and, optionally, one or more other conventional pharmaceutical adjuvants and administered enterally, e.g. orally, in the form of tablets, capsules, caplets, etc. or parenterally, e.g., intraperitoneally or intravenously, in the form of sterile injectable solutions or suspensions. The enteral and parenteral compositions may be prepared by conventional means.

The infusion solutions according to the present invention are preferably sterile. This may be readily accomplished, e.g. by filtration through sterile filtration membranes. Aseptic formation of any composition in liquid form, the aseptic filling of vials and/or combining a pharmaceutical composition of the present invention with a suitable diluent under aseptic conditions are well known to the skilled addressee.

The STAUROSPORINE DERIVATIVES may be formulated into enteral and parenteral pharmaceutical compositions containing an amount of the active substance that is effective for treating the diseases and conditions nemed hereinbefore, such compositions in unit dosage form and such compositions comprising a pharmaceutically acceptable carrier.

The STAUROSPORINE DERIVATIVES can be used alone or combined with at least one other pharmaceutically active compound for use in these pathologies. These active compounds can be combined in the same pharmaceutical preparation or in the form of combined preparations "kit of parts" in the sense that the combination partners can be dosed independently or by use of different fixed combinations with distinguished amounts of the combination partners, i.e., simultaneously or at different time points. The parts of the kit of parts can then, e.g., be administered simultaneously or chronologically staggered, that is at different time points and with equal or different time intervals for any part of the kit of parts. Non-limiting examples of compounds which can be cited for use in combination with STAUROSPORINE DERIVATIVES are cytotoxic chemotherapy drugs, such as cytosine arabinoside, daunorubicin, doxorubicin, cyclophosphamide, VP-16, or imatinib etc. Further, STAUROSPORINE DERIVATIVES could be combined with other inhibitors of signal transduction or other oncogene-targeted drugs with the expectation that significant synergy would result.

Examples of useful compositions are described in the European patents No. 0 296 110, No. 0 657 164, No. 0 296 110, No. 0 733 372, No. 0 711 556, No. 0 711 557.

The preferred compositions are described in the European patent No. 0 657 164 published on Jun. 14, 1995. The described pharmaceutical compositions comprise a solution or dispersion of compounds of formula I such as MIDOSTAURIN in a saturated polyalkylene glycol glyceride, in which the glycol glyceride is a mixture of glyceryl and polyethylene glycol esters of one or more C8-C18 saturated fatty acids.

Two manufacture processes of such compositions are described hereafter.

Composition A:

Gelucire 44/14 (82 parts) is melted by heating to 60° C. Powdered MIDOSTAURIN (18 parts) is added to the molten material. The resulting mixture is homogenised and the dispersion obtained is introduced into hard gelatin capsules of different size, so that some contain a 25 mg dosage and others a 75 mg dosage of the MIDOSTAURIN. The resulting capsules are suitable for oral administration.

Composition B:

Gelucire 44/14 (86 parts) is melted by heating to 60° C. Powdered MIDOSTAURIN (14 parts) is added to the molten material. The mixture is homogenised and the dispersion obtained is introduced into hard gelatin capsules of different size, so that some contain a 25 mg dosage and others a 75 mg dosage of the MIDOSTAURIN. The resulting capsules are suitable for oral administration.

Gelucire 44/14 available commercially from Gaftefossé; is a mixture of esters of C8-C18 saturated fatty acids with glycerol and a polyethylene glycol having a molecular weight of about 1500, the specifications for the composition of the fatty acid component being, by weight, 4-10% caprylic acid, 3-9% capric acid, 40-50% lauric acid, 14-24% myristic acid, 4-14% palmitic acid and 5-15% stearic acid.

A preferred example of Gelucire formulation consists of:
Gelucire (44/14): 47 g
MIDOSTAURIN: 3.0 g filled into a 60 mL Twist off flask
A Preferred Example of Soft Gel will Contain the Following Microemulsion:

| | |
|---|---|
| Cornoil glycerides | 85.0 mg |
| Polyethylenglykol 400 | 128.25 mg |
| Cremophor RH 40 | 213.75 mg |
| MIDOSTAURIN | 25.0 mg |
| DL alpha Tocopherol | 0.5 mg |
| Ethanol absolute | 33.9 mg |
| Total | 486.4 mg |

However, it should be clearly understood that it is for purposes of illustration only.

In a preferred embodiment this invention relates to use or method as described herein, wherein the daily effective amount of the compound of formula VII, is 100 to 300 mg, preferably 125 mg to 250 mg most preferably 220 to 230 mg, preferably 225 mg.

Most preferably the compound of formula VII, is administered once, twice or three times a day, for a total dose of 100 to 300 mg daily.

In a very preferred embodiment the compound of formula VII, is administered three times a day, for a total dose of 220 to 230 preferably 225 mg daily, and preferably at a dose per administration of 70 to 80 mg, preferably 75 mg.

In still another embodiment, this invention relates to an article of manufacture comprising packaging material, and N-[(9S,10R,11R,13R)-2,3,10,11,12,13-hexahydro-10-methoxy-9-methyl-1-oxo-9,13-epoxy-1H,9H-diindolo[1,2,3-gh: 3',2',1'-lm]pyrrolo[3,4j][1,7]benzodiazonin-11-yl]-N-methylbenzamide of the formula (VII) or a pharmaceutically acceptable salts thereof, contained within said packaging material, wherein said packaging material comprises label directions which indicate that said compound of formula (VII), or said pharmaceutically-acceptable salt, is to be administered to mammals suffering from allergic rhinitis, allergic dermatitis, drug allergy or food allergy, angioedema, urticaria, sudden infant death syndrome, bronchopulmonary aspergillosis, multiple sclerosis, or mastocytosis, in an amount from 50 to 500 mg, preferably 100 to 300 mg, preferably 125 mg to 250 mg, more preferably 220 to 230 mg, most preferably 225 mg following a specific dosage regimen to inhibit the development of the diseases and conditions mentioned hereinbefore.

Preferably the invention also relates to an article of manufacture wherein the compound of formula VII, is administered three times a day, for a total dose of 220 to 230 mg, preferably 225 mg daily, and preferably a dose of 70 to 80 mg, most preferably 75 mg, per administration for the treatment of hypereosinophilic syndrome or hypereosinophilic syndrome with resistance to imatinib. A preferred embodiment relates to an article of manufacture comprising softgel capsules containing 25 mg of the compound of formula VII.

The invention further pertains the combination of a STAUROSPORINE DERIVATIVE as described hereinbefore with imatinib for the treatment of the diseases and conditions described hereinbefore. The administration of such a combination may be affected at the same time, for instance in the form of a fixed, combined pharmaceutical composition or preparation, or sequentially or timely staggered. The administration of a STAUROSPORINE DERIVATIVE in a dosage form as described hereinbefore and of imatinib in its marketed form of GLEEVEC® in the US/GLIVEC® in Europe and with the dosages envisaged for these dosage forms is currently preferred.

The treatment of allergic rhinitis, allergic dermatitis, drug allergy or food allergy, angioedema, urticaria, sudden infant death syndrome, bronchopulmonary aspergillosis, multiple sclerosis, or mastocytosis with the above combination may be a so-called first line treatment, i.e. the treatment of a freshly diagnosed disease without any preceeding chemotherapy or the like, or it may also be a so-called second line treatment, i.e. the treatment of the disease after a preceeding treatment with imatrinib or a STAUROSPORINE DERIVATIVE, depending on the severity or stage of the disease as well as the over all condition of the patient etc.

The term "allergic rhinitis" as used herein means any allergic reaction of the nasal mucosa. Such allegic reaction may occur, e.g., perennially, e.g. vernal conjunctivitis, or seasonally, e.g., hay fever.

The term "allergic dermatitis" as used herein means especially atopic dermatitis, allergic contact dermatitis and eczematous dermatitis, but comprises, e.g., also seborrhoeic dermatitis, Lichen planus, urticaria and acne. Atopic dermatitis as defined herein is a chronic inflammatory skin disorder seen in individuals with a hereditary predisposition to a lowered cutaneous threshold to pruritus. It is principally characterized by extreme itching, leading to scratching and rubbing that in turns results in the typical lesons of eczema. Allergic contact dermatitis as defined herein is a form of dermatitis that is due to the allergic sensitization to various substances that produce inflammatory reactions in the skin of those who have acquired hypersensitivity to the allergen as a result of previous exposure to it.

The term "drug allergy or food allergy" as used herein pertains to an allergic reaction produced by a drug or ingested antigens, such as, for example, strawberries, milk or eggs.

The term "bronchopulmonary aspergillosis" relates to an infection of the lungs with *Aspergillus*.

The term "mastocytosis" as used herein, relates to systemic mastocytosis, for example mastocytoma, and also to canine mast cell neoplasms. Mastocytosis is a myeloproliferative disorder with limited treatment options and generally a poor prognosis. The pathogenesis of mastocytosis has been attributed to constitutive activation of the receptor tyrosine kinase KIT. In a large majority of mastocytosis patients, the deregulated tyrosine kinase activity of KIT is due to a mutation within the codon 816 of the protein (D816V) which also confers resistance to imatinib or imafinib mesylate, the latter being marketed as Gleevec® in the United States or Glivec® elsewhere, in vitro and in vivo.

Mast cells play an important role as the primary effector cells in the allergic disorders mentioned herein. Antigen-specific IgE-mediated degranulation of mast cells leads to the subsequent release of chemical mediators and multiple cytokines and to leukotriene synthesis. Furthermore, mast cells are involved in the pathogenesis of multiple sclerosis. Mast cell neoplasms occur in both humans and animals. In dogs, mast cell neoplasms are called mastocytomas, and the disease is common, representing 7%-21% of canine tumors. A distinction must be drawn between human mastocytosis, which is usually transient or indolent, and canine mast cell neoplasia, which behaves unpredictably and is often aggressive and metastatic. For instance, human solitary mastocytomas do not often metastasize; in contrast, 50% of canine mastocytomas behave in a malignant fashion, as estimated by Hottendorf & Nielsen (1969) after review of 46 published reports of tumors in 938 dogs.

Cancer in the pet population is a spontaneous disease. Pet owners, motivated by prolonging the quality of their animals' life, frequently seek out the specialized care and treatment of veterinary oncologists at private referral veterinary hospitals and veterinary teaching hospitals across the country. Therapeutic modalities of veterinary cancer patients are similar to humans, including surgery, chemotherapy, radiation therapy, and biotherapy. It has been estimated that there are 42 million dogs and approximately 20 million cats in the United States. Using crude estimates of cancer incidence, there are roughly 4 million new cancer diagnoses made in dogs and a similar number in cats made each year.

Cutaneous mast cell tumors in dogs are a common problem. Most mast cell tumors are benign and are cured with simple resection; however, if recurrent or metastatic to distant sites therapeutic options are limited. Treatment options for recurrent lesions can include external beam radiation therapy. For distant metastases or disseminated disease the use of Lomustine® and vinblastine containing chemotherapy protocols have demonstrated some benefit. Sites for metastases for mast cell tumors include skin, regional lymph nodes, spleen, liver, and bone marrow.

The KIT receptor's involvement in the pathogenesis of mastocytosis is suggested by the observation that several mutations resulting in constitutive activation of KIT have been detected in a number of mast cell lines. For instance, a point mutation in human c-KIT, causing substitution of Val for Asp816 in the phosphotransferase domain and receptor autoactivation, occurs in a long-term human mast cell leukemia line (HMC-1) and in the corresponding codon in two rodent mast cell lines. Moreover, this activating mutation has been identified in situ in some cases of human mastocytosis. Two other activating mutations have been found in the intracellular juxtamembrane region of KIT, i.e. the Val560Gly substitution in the human HMC-1 mast cell line, and a seven amino acid deletion (Thr573-His579) in a rodent mast cell line called FMA3.

It can be shown by established test models and especially those test models described herein that the STAUROSPORINE DERIVATIVES or in each case a pharmaceutically acceptable salt thereof, result in an effective prevention or, preferably, treatment of at least one of the diseases mentioned herein. The person skilled in the pertinent art is fully enabled to select a relevant test model to prove the hereinbefore and hereinafter indicated therapeutic indications and beneficial effects. The pharmacological activity may, for example, be demonstrated in a clinical study or in the test procedure as essentially described hereinafter.

EXAMPLE 1

This Example demonstrates the in vitro effects of the STAUROSPORINE DERIVATIVES on the SCF-dependent development of cultured human mast cell growth generated from CD34$^+$ cord blood cells using the culture system described by Kinoshita T, Sawai N, et al in Blood 1999, 94, 496-508. More than 90% of the isolated cells were CD34-positive according to the flow cytometric analysis.

Reagents and Antibodies

The STAUROSPORINE DERIVATIVES are solubilized in DMSO at a concentration of $10^{-2}$ M and stored at $-80°$ C. All-trans retinoic acid (Sigma) is dissolved in ethanol at a concentration of $10^{-2}$ M, and stored in light-protected vials at $-80°$ C. Purified mAb for tryptase (MAB1222) can be purchased from Chemicon International Inc., CA. For the flow cytometric analysis, the mAbs for CD34 (8G12, FITC) and CD11b (Leu15, PE) are purchased from Becton Dickinson Immunocytometry Systems (Mountain View, Calif.), and the mAb for CD41 (SZ22, FITC) from Immunotech S.A. (Marseilles, France). The mAb for glycophorin A (GPA, JC159, FITC) can be obtained from Dako (Glostrup, Denmark). For western blotting and immunoprecipitation, the mAbs for c-kit (NU-c-kit) and for phosphotyrosine (4G10) can be purchased from Nichirel and Upstate Biotechnology, Inc (Lake Placid, N.Y.), respectively.

Suspension Cultures

Serum-deprived liquid cultures are carried out in 24-well culture plates (#3047; Becton Dickinson). Twenty thousand $CD34^+$ cells are cultured in each well containing 2 mL of α-medium supplemented with 1% BSA, 300 µg/mL fully iron-saturated human transferrin (approximately 98% pure, Sigma), 16 µg/mL soybean lecithin (Sigma), 9.6 µg/mL cholesterol (Nakalai Chemicals Ltd., Japan) and 20 ng/mL of SCF, 10 ng/mL of GM-CSF, 2 U/mL of EPO, 10 ng/mL of TPO, different concentrations of a STAUROSPORINE DERIVATIVE, alone or in combination. In order to examine the effects of a STAUROSPORINE DERIVATIVE on the SCF-dependent development of mast cells, 10-wk cultured cells grown with 20 ng/mL of SCF from $CD34^+$ cord blood cells are used as target cells. Five to ten×$10^4$ 10-wk cultured cells are incubated for 2 wk in 24-well culture plates containing 20 ng/mL of SCF with or without various concentrations of a STAUROSPORINE DERIVATIVE. The plates are incubated at 37° C. in a humidified atmosphere flushed with a mixture of 5% $CO_2$, 5% $O_2$, and 90% $N_2$. When the culture continued unUil 4 wk, half of the culture medium is replaced every 2 wk with fresh medium containing the factor(s). The number of viable cells is determined by a trypan-blue exclusion test using a hemocytometer.

Clonal Cell Cultures

The mast cell colony assay is carried out in 35-mm Lux suspension culture dishes (#171099; Nunc, Ill.). The culture consisted of 10-wk cultured cells (4,000 cells/mL) grown with 10 ng/mL of SCF, α-medium, 0.9% methylcellulose (Shinetsu Chemical, Japan), 1% BSA, 300 µg/mL of fully iron-saturated human transferrin, 16 µg/mL of soybean lecithin, 9.6 µg/mL of cholesterol and 100 ng/mL of SCF with or without $10^{31\ 6}$ M of a STAUROSPORINE DERIVATIVE. Dishes are incubated at 37° C. in a humidified atmosphere flushed with a mixture of 5% $CO_2$, 5% $O_2$, and 90% $N_2$. After 4 wk, aggregates consisting of 30 or more cells are scored as mast cell colonies, and those consisting of 10 to 29 cells as mast cell clusters. Thirty individual colonies and clusters are lifted, and stained with the anti-tryptase mAb or mouse IgG1 using the alkaline phosphatase-anti-alkaline phosphatase (APAAP) technique. Almost all of the constituent cells are positive for tryptase.

Cytochemical and Immunologic Stainings

The cultured cells are spread on glass slides using a Cytospin II. Cytochemical reaction with peroxidase (POX) is performed by the conventional method. Reaction with mAb against tryptase is detected using the APMP method (Dako APAAP Kit System, Dako Corp., CA), as described by F. Ma, K. Kolke, et al. in Br. J. Haematol. 1998, 100, 427-35.

Immunoprecipitation and Western Blotting

Immunoprecipitation and western blotting are performed, as described by T. Kamijo, K. Koike, et al. in Leuk. Res. 1997, 21, 1097-106.

Flow Cytometric Analysis

For the analysis of surface markers on the cultured cells, 1-2×$10^5$ cells are collected in plastic tubes and incubated with appropriately diluted FITC- or PE-mAb, as described by Kinoshita T, Sawai N, et al in Blood 1999, 94, 496-508. The cells are washed twice, after which their surface markers are analyzed with the FACScan flow cytometer. Viable cells are gated according to their forward light scatter characteristics and side scatter characteristics. The proportion of positive cells is determined by comparison to cells stained with FITC- or PE-conjugated mouse isotype-matched Ig.

Detection of Cellular Apoptosis

The analysis of cellular apoptosis is carried out by a flow cytometric analysis using propidium iodide (PI, Sigma) according to the procedure described by N. Sawai, K. Koike, et al in Stem Cells. 1999, 17, 45-53. In order to reduce cells undergoing apoptosis, necrosis or already dead, a percoll gradient centrifugation can be utilized. Ten-wk cultured cells are layered on 27% Percoll (Sigma) in α-medium and 54% Percoll in PBS. After centrifugation, the cells are collected from the interface of the two differtent concentrations of Percoll solution, washed with PBS and treated with 1 mL of Ortho PermeaFix™ for 40 min at room temperature. The cells are then incubated with DNase-free RNase (Sigma) for 15 min at 37° C., and stained with PI for 15 min. The DNA content of 2×$10^4$ cells is monitored with a flow cytometer. The 10-wk cultured cells (2×$10^6$) exposed to SCF or SCF and a STAUROSPORINE DERIVATIVE are lysed for 10 min on ice in 100 µL hypotonic lysis buffer[10 mM Tris (pH 7.5), 10 mM EDTA, pH 8.0, 0.5% Triton X-100]. After centrifugation for 10 min at 14,000 g, the supernatant is transferred to a new tube, and treated with 0.2 mg/mL RNase A (Sigma) and 0.2 mg/mL Proteinase K (Sigma). DNA is precipitated with 120 µL isopropanol and 20 µL 5M NaCl overnight at −20° C. After centrifugation at 14,000 g, the pellets are dried, dissolved in 20 µL Tris-EDTA, and then samples are analyzed by gel electrophoresis in 2% agarose and ethidium bromide staining.

Assay of Histamine, Tryptase and Cytokine Levels

Histamine concentrations in cell lysates obtained by the treatment of the cultured cells with 0.5% Nonidet P-40 and in supernatant are measured by Histamine Radioimmunoassay (RIA) Kit (Immunotech), as described in Kinoshita T, Sawai N, et al in Blood 1999, 94, 496-508.

Statistical Analysis

All experiments should be carried out at least three times. To determine the significance of difference between two independent groups, the unpaired t-test can be used, or the Mann-Whitney-U test when the data are not normally distributed.

EXAMPLE 2

Methods

Reagents: Novartis Pharma; Basel, Switzerland: PKC412 or MIDOSTAURIN for use in these experiments. Fresh 10 mM stock solutions of the inhibitor are made before each experiment by dissolving compound in 1 ml DMSO (dimethyl-sulfoxide).

Antibodies: A polyclonal rabbit anti-KIT antibody (c-kit Ab-1) is used at a dilution of 1:500 (c-kit Ab-1; Oncogene, Cambridge, Mass.). An anti-phosphotyrosine antibody (PY20) is used at a dilution of 1:1000 (PY20 Transduction Laboratories; Lexington, Ky.). Peroxidase conjugated goat anti-mouse antibody is used at a dilution of 1:5000 and goat anti-rabbit antibody at a dilution of 1:10,000 (Pierce; Rockford, Ill.).

Cell lines: BR and C2 canine mastocytoma cells lines are obtained from Dr. George Caughey (University of California at San Francisco, San Francisco, Calif.). Both cell lines are maintained in DMEM supplemented with 2% bovine calf, 1 mM L-glutamine, 12.5 mM HEPES (pH 7.5), 0.25 mg/ml Histidine, 1% Penicillin-Streptomycin and 1% fungizone. The BR and C2 cells are derived from canine mast cell tumors and are originally established in long-term culture after initial passaging in immunodeficient mice (DeVinney R et al., Am J Respir Cell Mol Biol 1990; 3(5):413-420; Lazarus S C et al., Am J Physiol 1986; 251(6 Pt 1):C935-C944). The BR cell line has a point mutation (T1752C) resulting in a Leucine to Proline substitution at amino acid 575 auxtamembrane domain). The C2 cell line has an internal tandem duplication (ITD) of the KIT juxtamembrane region. The translation of this ITD results in reduplication of amino acid residues at the 3' end of exon 11 (London C A et al., Exp Hematol 1999; 27(4):689-697; Ma Y et al., J Invest Dermatol 1999; 112(2): 165-170).

Proliferation Assays: Cells are added to 96 well plates at a density of 40,000 cells/well in normal culture media and varying concentrations of SALT I. Proliferation is measured at 48-72 hours using an XTT-based assay (Roche Molecular Biochemicals; Indianapolis, Ind.). (Heinrich M C et al., Blood 2000; 96(3):925-932).

Protein Lysates: BR and C2 cells are washed×2 in PBS and then quiesced in Optimem (Gibco-BRL) at 37° C. for approximately 18 hours. Cells are then incubated for 90 minutes in the presence of various concentrations of PKC412. Following this incubation, the cells are pelleted and lysed using 100-250 µl of protein lysis buffer (50 mM Tris, 150 mM NaCl, 1% NP-40, 0.25% Deoxycholate, with addition of the inhibitors aprotinin, leupeptin, pepstatin, PMSF, and sodium orthovanadate [Sigma]). Western immunoblot analysis is performed as previously described (Hoatlin M E et al., Blood 1998; 91(4):1418-1425; Heinrich M C et al., Blood 2000; 96(3):925-932).

EXAMPLE 3

COMPOUND I Inhibits the Constitutively Activated KIT Kinase Associated with Canine Mast Cell Tumors To test the efficacy of COMPOUND I in inhibiting the kinase activity of mutant forms of canine KIT we use two cells lines (BR and C2) that express two different constitutively activated KIT isoforms. The KIT mutations in these cell lines are both located in the juxtamembrane domain and are homologous to mutations seen in human Gastrointestinal Stromal Tumors (GISTs) (Lux M L et al., Am J Pathol 2000; 156(3):791-795; Rubin B P et al., Cancer Res 2001; 61(22): 8118-8121). Lysates prepared from BR or C2 cells are probed with an anti-P-Tyr antibody and KIT receptor activation is assessed by measuring autophosphorylation. As reported previously, KIT autophosphorylation in these cells is observed in the absence of SLF (Ma Y et al., J Invest Dermatol 1999; 112(2):165-170; Ma Y et al., Journal of Investigative Dermatology 2000; 114(2):392-394). Inhibition of KIT autophosphorylation by PKC412 is dose dependent with complete inhibition observed using 10 and 1.0 µM doses. Near complete inhibition is seen using a dose of 0.1 µM. Limited autophosphorylation of c-kit is seen using 0.001-0.01 µM doses of PKC41 2. Thus, PKC412 not only inhibits the autophosphorylation of the mutated c-kit receptor in these cells, but also is a more potent inhibitor of this mutated receptor than it is of the wild type c-kit receptor ($IC_{50}$ 100-200 nM). To determine if PKC412 modulated expression of KIT protein, the membrane was stripped and reprobed with an anti-c-kit antibody. There was no change in expression of c-kit protein in PKC412 treated cells. Therefore, PKC412 decreases autophosphorylation of mutant canine KIT polypeptide by inhibiting KIT kinase activity rather than by down regulating expression of KIT protein.

EXAMPLE 4

COMPOUND I Inhibits the Proliferation of Cell Lines of Canine Mast Cell Tumors To test the biologic effect of inhibiting the kinase activity of a mutant c-kit receptor, BR or C2 cells are cultured for 48-72 hours in the presence of various concentrations of PKC412. At inhibitor concentrations of 0.1-10 µM, proliferation is decreased by 90-95% compared to cells treated with media only. Partial inhibition of proliferation is seen at doses of 0.001-0.01 µM PKC412. Therefore, PKC412 inhibits proliferation of BR and C2 cells with the same dose response range as seen for inhibition of receptor autophosphorylation. Morphologic observations of the inhibitor treated cells revealed changes consistent with apoptosis.

EXAMPLE 5

Example of a Prospective Case Series of Pet Dogs with Measurable Cutaneous Mast Cell Tumors The study patients are pet dogs with measurable and histologically confirmed mast cell tumors. Cases are limited to those with measurable lesions amenable to biopsy.

Eligibility Criteria Are:

histologically confirmed measurable cutaneous mast cell tumors cases will require serial biopsy with 2 mm Keyes punch before and during therapy histological grade (II-intermediate or III-poorly differentiated)

performance status 0 or 1 (Modified Karnofsky—Table 1)

informed owner consent (a) Exclusion Criteria Are:

concurrent cytotoxic chemotherapy prednisone and non-steroidal anti-inflammatory drugs may not be initiated within 30 days of the study; if prednisone or non-steroidal anti-inflammatory drugs have been administered for greater than 30 days they may be continued abnormal serum bile acid test (liver function)

TABLE 1

Performance Status (Modified Karnofsky)

| Grade | Description |
|---|---|
| 0 | Normal activity |
| 1 | Restricted activity; decreased activity from pre-disease status |
| 2 | Compromised; ambulatory only for vital activities; consistently defecates and urinates in acceptable areas |
| 3 | Disabled; must be force fed; unable to confine urination and defecation to acceptable areas |
| 4 | Dead |

Pretreatment evaluation of all cases include physical examination, complete blood count, buffy coat, serum biochemistry, urinalysis, serum bile acids (fasting and post-prandial), documentation of regional lymph node size, abdominal radiographs, and abdominal ultrasound. The treatment regimen is 25 mg/kg PO QD×60 days of MIDOSTAURIN.

Treatment is continued in all cases for 60 days unless disease progression is noted. In cases experiencing partial response or complete response ongoing therapy for an additional 60 days may be considered. Cases successfully completing therapy are eligible for repeat entry to study.

TABLE 2

Treatment and Clinical Evaluation Plan.

| Action | Day 0 | Day 7 | Day 14 | Day 28 | q14 days |
|---|---|---|---|---|---|
| Clinical Staging[1] | X | | | X | X |
| Physical Examination | X | X | X | X | X |

TABLE 2-continued

Treatment and Clinical Evaluation Plan.

| Action | Day 0 | Day 7 | Day 14 | Day 28 | q14 days |
|---|---|---|---|---|---|
| Measurement of tumor burden[2] | X | X | X | X | X |
| Start MIDOSTAURIN 25 mg/kg QD | X | | | | |
| Pharmacokinetics[3] | X | | | | |
| Incisional biopsy[4] | X | | | X | |
| Repeat Staging | | | | X | |

[1]Initial staging consists of physical examination, CBC, buffy coat, serum biochemistry, liver function tests (serum bile acids), urinalysis, abdominal radiographs, and abdominal ultrasound. Re-evaluation of may consist of physical examination and measurement of tumor burden alone or repeat clinical staging.
[2]Tumor burden is measured at day 0, 7, 14, 28 and then every 14 days. Treatment response will be defined against measurable cutaneous lesion(s) and other lesions identified at staging (CR, PR, SD, PD - defined below).
[3]Collection of plasma from the first 5 entered cases is undertaken at 0, 0.5, 1, 2, 5, 8, 12, 16, 24 hours following first dose of MIDOSTAURIN.
[4]Incisional biopsy from defined measurable lesion(s) will be collected on day 0 and 28 from all cases. Additional biopsies are collected at the time of partial response (PR) and after complete objective response (CR).

The efficacy of a STAUROSPORINE DERIVATIVE is assessed against measurable cutaneous mast cell tumors, using clinical endpoints. Biological endpoints may be taken from serial biopsies collected from cutaneous tumors and from blood samples available through the treatment course.

Clinical endpoints include response rate of measurable tumors, objective response against measurable tumor, and time to progression of measurable tumor. All adverse side effects will be recorded.

"Objective Tumors Responses", as defined below, are observed under treatment with a STAUROSPORINE DERIVATIVE and indicate efficacy of the treatment regimen.

In particular, Complete Responses and Partial Responses to treatment with a STAUROSPORINE DERIVATIVE may be observed. Furthermore, it may be observed that more animals obtaining treatment show Stable Disease, while less treated animals show Progressive Disease. Also, it may be observed that less animals obtaining treatment show Relapse of disease as compared to non-treated animals. Time To Progression, Duration of Remission, and Survival may increase in animals under treatment with a STAUROSPORINE DERIVATIVE.

"Complete Response (CR)" is defined as disappearance of all clinical evidence of cancer and of any signs related to the cancer.

"Partial Response (PR)" is defined as a 50% or greater decrease In the sum of the products of measurements for representative lesions, without an increase in size of any lesions or appearance of any new lesions.

"Stable Disease (SD)" is defined as no response or a response of less than that defined for partial response or progressive disease without appearance of any new lesions or worsening of clinical signs.

"Progressive Disease (PD)" is defined as an unequivocal increase of at least 50% in the size of any measurable lesion or appearance of new lesions.

"Relapse (R)" is defined as appearance of new lesions or reappearance of old lesions in dogs that had had a complete response; in dogs that had had only a partial response, relapse was defined as at least a 50% increase in the sum of the products of measurements of representative lesions, compared with measurements obtained at the time of maximum response.

"Time To Progression (TTP)" is reported from day 0 of the protocol. TTP will be defined as the number of days start of therapy (from day 0) to relapse (R).

"Duration of Remission" is defined as the number of days from the objective response (PR or CR) to relapse.

"Survival" is defined as the number of days from the start of treatment with a STAUROSPORINE DERIVATIVE to death. Cause of death will be noted but may include disease progression, toxicity, and other.

EXAMPLE 6

A 48-year-old woman presented with fever, purpura, spienomegaly, diarrhea, and transfusion-dependent anemia and thrombocytopenia. The initial white blood cell count was 20,000/mm3 with myeloid immaturity and dysplasia, and 8% blasts. A bone marrow biopsy showed 5-10% blasts, trilineage dysplasia and 30-50% mast cells. Testing of the peripheral blood revealed heterozygosity for the D816V KIT mutation and wild-type FLT-3. She was diagnosed with systemic mastocytosis with an associated mixed myelodysplastic/myeloproliferative syndrome. Two months after presentation, her disease progressed with 30-40% circulating mast cells. She was supported with red blood cell and platelet transfusions, antihistamine blockade, and cromolyn sodium. She developed progressive liver dysfunction, severe ascites, and portal vein thrombosis. Treatment with PKC412 was Initiated at a dose of 100 mg twice daily orally (28-day cycles). At the start of therapy, serum histamine levels ranged from 6910-7336 ng/dL (normal <100 ng/dL) and the serum tryptase was >200 ug/L (normal <10.9 ug/L).

By End of Cycle 1: Partial Response (Critiera of Valent et al, *Leuk Res.* 2003; 27:635-641)
  Karnofsky performance status improved from 20% to 70%
  Improvement In diarrhea and marked reduction in ascites; 1 portal vein thrombosis recanalized
  Peristent transfusion dependent anemia and thrombocytopenia
  Total/direct bilirubin decreased from 4.8/2.8 to 2.1/1.1 mg/dL; LDH decreased from 769 to 239 IU/L
  Serum histamine decreased from 7000 to 1000 ng/dL; serum tryptase remained elevated >200 ug/L
  Peripheral blood: mast cell numbers decreased from 40-50% to <10%; increasing myeloid maturity
  Bone marrow: no changes in clusters of mast cells by IPOX; blasts decreased to <5%

After 1 month of PKC412 therapy, the patients Karnofsky performance status increased from 20% to 70%, liver function and ascites markedly Improved, and the portal vein recanalized. By day 32 of treatment, the patient exhibited a normal white blood cell count, <5% circulating mast cells and almost complete resolution of myelold immaturity. A bone marrow biopsy at this time showed reduction in blasts to <5% with persistent mast cells and dysplasia. The serum histamine level declined to 1031 ng/dL; however, the serum tryptase remained elevated.

By End of Cycle 2: Maintenance of Partial Response
  Maintenance of improved clinical symptoms and Karnofsky performance status
  Transient platelet-transfusion independence for 2-3 weeks (platelets to 20,000-25,000/mm3)
  Further improvement in total/direct bilirubin: decrease from 2.1/1.1 to 1.3/0.7 mg/dL
  Serum histamine remained in 800-1200 ng/dL range; serum tryptase remained elevated >200 ug/L
  Bone marrow: no significant change in clusters of mast cell clusters; blasts to 10-15%
  Peripheral blood: mast cell numbers remain <10%; increasing myeloid immaturity and blasts After 2 months of PKC412 therapy, she remains clinically stable with a decreased platelet transfusion requirement.

By End of Cycle 3: Disease Progression

Karnofsky performance status began to decline; increasing hepatosplenomegaly, ascites, bilirubin PKC412 dose increased to 75 mg po tid on day #91

PKC412 stopped on day #102, due to progressive disease with worsening organomegaly, bilirubin (total 14 mg/dL), and increasing peripheral blood blasts (likely progression of mast cell leukemia with associated clonal, hematological non-mast cell lineage disease)

Serum histamine began increasing again, to 2525 ng/dL; patient expired on day #111.

PKC412 was well tolerated without any significant adverse events. The partial response to PKC412 in this advanced case of mast cell leukemia suggests that this compound is active in systemic mastocytosis.

The invention claimed is:

1. A method of treating mastocytosis, which comprises administering a therapeutically effective amount of a compound of formula (VII)

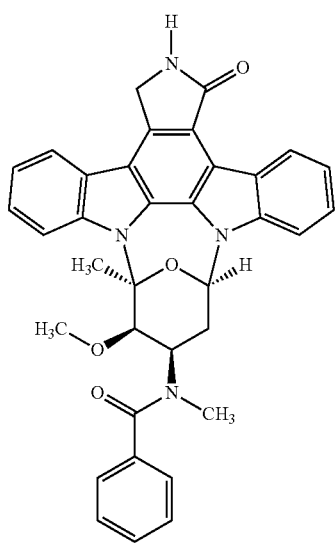

(VII)

or a pharmaceutically acceptable salt thereof,
to a human patient suffering from mastocytosis, wherein the human patient ha KIT tyrosine kinase receptor with a D816V mutation.

2. A method according to claim 1, wherein the therapeutically effective amount of the compound of formula VII is administered to a mammal subject 7 to 4 times a week or about 100% to about 50% of the days in the time period, for a period of from one to six weeks, followed by a period of one to three weeks, wherein the compound is not administered and this cycle being repeated for from 1 to several cycles.

3. A method according to claim 1, wherein the therapeutically effective amount of the compound of formula VII is 100 to 300 mg daily.

4. A method according to claim 1, wherein the compound of formula VII is administered one, two or three times a day, for a total dose of 100 to 300 mg daily.

5. A method according to claim 1, wherein the compound of formula VII is administered three times a day, for a total dose of 225 mg daily.

6. A method according to claim 1, wherein the compound of formula VII is administered orally.

7. A method according to claim 1, wherein the compound of formula VII is administered as a microemulsion, soft gel or solid dispersion.

8. A method according to claim 1, wherein up to 125 mg per day of the compound of formula VII is administered.

9. A method according to claim 4, wherein the compound of formula VII is administered orally.

10. A method according to claim 9, wherein the compound of formula VII is administered as a microemulsion.

11. A method of treating mastocytosis with resistance to imatinib, which comprises administering a therapeutically effective amount of a compound of formula (VII)

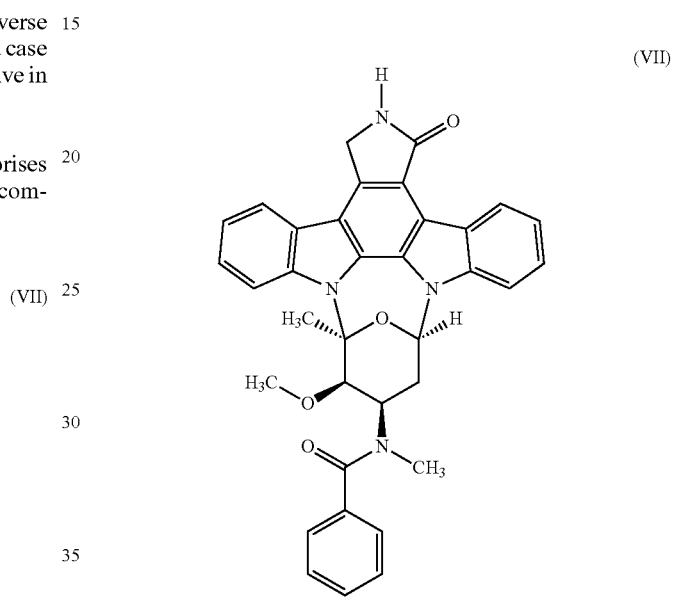

(VII)

or a pharmaceutically acceptable salt thereof,
to a patient suffering from mastocytosis with resistance to imatinib and wherein the patient ha KIT tyrosine kinase receptor with a D816V mutation.

12. A method according to claim 11, wherein the therapeutically effective amount of the compound of formula VII is administered to a mammal subject 7 to 4 times a week or about 100% to about 50% of the days in the time period, for a period of from one to six weeks, followed by a period of one to three weeks, wherein the compound is not administered and this cycle being repeated for from 1 to several cycles.

13. A method according to claim 11, wherein the therapeutically effective amount of the compound of formula VII is 100 to 300 mg daily.

14. A method according to claim 11, wherein the compound of formula VII is administered one, two or three times a day, for a total dose of 100 to 300 mg daily.

15. A method according to claim 11, wherein the compound of formula VII is administered orally.

16. A method according to claim 11, wherein the compound of formula VII is administered as a microemulsion, soft gel or solid dispersion.

17. A method according to claim 11, wherein up to 125 mg per day of the compound of formula VII is administered.

18. A method according to claim 14, wherein the compound of formula VII is administered orally.

19. A method according to claim 18, wherein the compound of formula VII is administered as a microemulsion.

* * * * *

UNITED STATES PATENT AND TRADEMARK OFFICE
CERTIFICATE OF CORRECTION

PATENT NO. : 8,575,146 B2  
APPLICATION NO. : 10/560669  
DATED : November 5, 2013  
INVENTOR(S) : Steven Coutre Page 1 of 1

It is certified that error appears in the above-identified patent and that said Letters Patent is hereby corrected as shown below:

In the Claims

Column 35, Line 49, Claim 1, replace "ha" with --has--  
Column 36, Line 40, Claim 11, replace "ha" with --has--

Signed and Sealed this  
Eleventh Day of March, 2014

Michelle K. Lee  
*Deputy Director of the United States Patent and Trademark Office*